US010226374B2

(12) United States Patent
Hardcastle et al.

(10) Patent No.: US 10,226,374 B2
(45) Date of Patent: Mar. 12, 2019

(54) CERVICAL BRACE

(71) Applicant: CERVICAL CHINUP PTY LTD, Osborne Park (AU)

(72) Inventors: Philip Hobson Hardcastle, Cottesloe (AU); Matthew Peter Oldakowski, Applecross (AU); Intan Camellia Watono Oldakowska, Applecross (AU); Brandon Jin Siew Liew, North Sydney (AU)

(73) Assignee: CERVICAL CHINUP PTY LTD, Osborne Park (AU)

( * ) Notice: Subject to any disclaimer, the term of this patent is extended or adjusted under 35 U.S.C. 154(b) by 331 days.

(21) Appl. No.: 14/712,453

(22) Filed: May 14, 2015

(65) Prior Publication Data

US 2015/0245940 A1 Sep. 3, 2015

Related U.S. Application Data

(63) Continuation-in-part of application No. PCT/AU2013/001321, filed on Nov. 15, 2013.

(51) Int. Cl.
*A61F 5/055* (2006.01)
*A61F 5/058* (2006.01)
(Continued)

(52) U.S. Cl.
CPC .......... *A61F 5/055* (2013.01); *A61F 5/05883* (2013.01); *A63B 21/026* (2013.01);
(Continued)

(58) Field of Classification Search
CPC .... A61F 5/04; A61F 5/05; A61F 5/055; A61F 5/05883
(Continued)

(56) References Cited

U.S. PATENT DOCUMENTS

| 2,820,455 A | 1/1958 | Hall |
| 2,904,040 A | 9/1959 | Hale |

(Continued)

FOREIGN PATENT DOCUMENTS

| GB | 2049436 A | 12/1980 |
| GB | 2049436 | 12/1982 |

(Continued)

OTHER PUBLICATIONS

International Search Report and Written Opinion for related international patent application No. PCT/AU2013/001321, dated Feb. 5, 2014, in 8 pages.

(Continued)

*Primary Examiner* — Keri J Nelson
(74) *Attorney, Agent, or Firm* — K&L Gates LLP

(57) ABSTRACT

A neck support apparatus (10) has a base portion (21) for positioning on the torso (18) of the user (11) and a support portion (23) extending from the base portion and having a rest (25) upon which the mandible (17)) of the user (11) can rest when the head (13) of the user is at the forwardmost tilted position. The rest (25) has two rest members (27) configured to receive the mandible (17), typically adjacent the underside of the posterior mandibles (17a) of the user (11). The support portion (23) further comprises two struts (31) which are mounted on the base portion (21) and on which the rest members (27) are mounted. The two struts (31) are adapted to be disposed angularly with respect to each other.

19 Claims, 29 Drawing Sheets

(51) Int. Cl.
*A63B 23/025* (2006.01)
*A63B 21/02* (2006.01)
*A63B 21/04* (2006.01)
*A63B 21/00* (2006.01)
*A63B 71/06* (2006.01)

(52) U.S. Cl.
CPC ...... *A63B 21/0442* (2013.01); *A63B 21/4005* (2015.10); *A63B 21/4025* (2015.10); *A63B 23/025* (2013.01); *A61F 2250/0004* (2013.01); *A63B 71/0622* (2013.01); *A63B 2210/50* (2013.01); *A63B 2220/17* (2013.01)

(58) Field of Classification Search
USPC ...................................... 602/17, 18
See application file for complete search history.

(56) References Cited

U.S. PATENT DOCUMENTS

| | | | |
|---|---|---|---|
| 5,088,482 A | 2/1992 | McGuinness | |
| 5,289,829 A * | 3/1994 | Roehrig | A61F 5/56 128/848 |
| 5,501,646 A | 3/1996 | Miller | |
| 7,371,222 B2 * | 5/2008 | Heinz | A61F 5/055 128/DIG. 23 |
| 7,789,843 B2 * | 9/2010 | Ray | A61F 5/055 128/845 |
| 8,191,553 B2 * | 6/2012 | Haworth | A61F 5/055 128/845 |
| 8,259,625 B2 | 9/2012 | Zhan | |
| 2002/0068889 A1 | 6/2002 | Bonutti | |
| 2011/0288459 A1 * | 11/2011 | Jenkins, III | A61F 5/055 602/18 |

FOREIGN PATENT DOCUMENTS

| | | |
|---|---|---|
| WO | 1999/043275 A1 | 9/1999 |
| WO | 2009/043275 | 4/2009 |
| WO | 2009/096895 | 8/2009 |
| WO | 2009/096895 A1 | 8/2009 |

OTHER PUBLICATIONS

Patent Examination Report dated Mar. 1, 2016 for related AU Patent Application No. 2015202914 in 7 pages.
International Preliminary Report on Patentability for related PCT/AU2013/001321, dated Mar. 3, 2015, in 21 pages.

* cited by examiner

CERVICAL BRACE

TECHNICAL FIELD

The present invention relates to an apparatus for supporting the head of a user.

More particularly, the invention is concerned with apparatus operable to resist forward tilting of the head of the user beyond a predetermined point to thereby afford support for the neck of the user.

The invention has been devised particularly, although not necessarily solely, in relation to provision of posture support for a use. The apparatus may function as a neck brace which are also known as cervical brace

BACKGROUND ART

The following discussion of the background art is intended to facilitate an understanding of the present invention only. The discussion is not an acknowledgement or admission that any of the material referred to is or was part of the common general knowledge as at the priority date of the application.

The human neck comprises of seven cervical vertebrae (bones) known in its entirety as the cervical spine. The cervical vertebrae form the uppermost portion of the vertebral column or spine. The cervical spine is also comprised of soft tissue including muscles and ligaments.

The neck is one of the most susceptible portions of the living body that is vulnerable to injury. The cervical spine is encapsulated in a small volume of soft tissue, which is utilized to prioritise mobility of the appendage over stability. Typical use of the neck requires an extensive range of motion.

Minor injuries to the neck tend to be based upon stress sustained to the soft tissue, leading to a neck sprain or neck strain. Major injuries to the neck tend to involve direct damage to the cervical spine, such as fractures, which can lead to loss of feeling, paralysis or death.

Treatment of an injured neck typically comprises of complete immobilisation and stabilisation of the head and neck in order to prevent further injury. Immobilisation and stabilisation should continue until the cervical vertebrae and/or soft tissue are healed. After this point, physical therapy is typically administered to the victim until the neck is able to self-stabilise without external assistance.

Immobilisation and stabilisation of the neck is achieved by using a neck brace or a neck collar. The choice of immobilisation and stabilisation apparatus is based upon the requirements of the patient. For major injuries, a rigid apparatus is required to completely immobilise and stabilise the neck, while minor injuries only require a soft and flexible apparatus for assisting in the stability of the neck.

Currently, neck braces are designed to immobilise and stabilise the neck. This purpose ensures that neck braces are rigid and disallow any movement. For minor neck injuries, patients would utilize soft collars due to their ability to assist weak cervical soft tissue in supporting and stabilising the neck while allowing mobility of the neck.

Both neck braces and collars have the disadvantage of not allowing patients who have minor soft tissue injury or who have recently recovered from major cervical vertebrae and/or soft tissue injury to engage in active exercise, which may be beneficial during the physical therapy phase of treatment.

Furthermore, known neck braces and collars typically have further disadvantages of not being cosmetically pleasing, and also being invasive and uncomfortable to wear. Consequently, patients might not wear the neck braces and collars as prescribed, which may contribute to their ineffectiveness in treating neck injury in some cases.

It is against this background that the present invention has been developed.

SUMMARY OF INVENTION

According to a first aspect of the invention, there is provided a support apparatus comprising a base portion for positioning on a part of the body of a user and a support portion extending from the base portion and adapted to engage a further part of the body of the user, whereby the base portion and the support portion co-operate to resist forward tilting of the head of the user beyond a predetermined point to thereby afford support for the neck of the user, the support portion comprising at least one strut to support the head of the user at a forwardmost tilted position.

Preferably, the support portion further comprises a rest upon which the head of the user can rest when at the forwardmost tilted position, the rest being mounted on said at least one strut.

Preferably, the rest is configured to receive and support the mandible of the user. With this arrangement, the underside of the jaw of the user would be received and supported on the rest.

In one arrangement, the rest may comprise two rest members upon and between which the mandible of the user can rest, the two rest members each being mounted on a respective one of the two struts.

In another arrangement, the rest may comprise a single rest member supported by and extending between the two struts In yet another arrangement, the rest may comprise two rest portions selectively movable between first and second conditions, wherein in the first condition the two rest portions cooperate to receive and support the mandible of the user and wherein in the second condition the two rest portions are in spaced apart relation to facilitate placement of the support portion on the user.

The two rest portions may be adapted to be releasable connected together in the first condition to provide an integrated rest structure to receive and support the mandible of the user, the integrated rest structure being supported by and extending between the two struts.

Preferably, the support portion comprises two struts.

In one arrangement, the rest may comprise two rest members upon and between which the mandible of the user can rest, the two rest members each being mounted on a respective one of the two struts.

In another arrangement, the rest may comprise a rest member supported by and extending between the two struts In yet another arrangement, the rest may comprise two rest portions selectively movable between first and second conditions, wherein in the first condition the two rest portions cooperate to receive and support the mandible of the user and wherein in the second condition the two rest portions are in spaced apart relation to facilitate placement of the support portion on the user.

The two rest portions may be adapted to be releasable connected together in the first condition to provide an integrated rest structure to receive and support the mandible of the user, the integrated rest structure being supported by and extending between the two struts.

The two struts may be adapted to be disposed angularly with respect to each other, whereby in use the two struts can extend upwardly and inwardly towards the mandible of the user. This arrangement is advantageous as it facilitates support for, and positioning of, the two rest members in a manner which does not adversely obstruct the field of vision of the user. In particular, the arrangement facilitates support for, and positioning of, the two rest members in a manner which is less intrusive and more aesthetically pleasing than current neck supporting devices. Furthermore, it is believed that the arrangement is neither too bulky nor cumbersome aesthetically as to constitute a deterrent to use of the support apparatus.

Preferably, the support portion is adjustable to accommodate the anatomy or physical characteristics of the user; typically, the size and configuration of the head of the user as well as the neck length of the user.

The adjustability of the support portion may involve the struts being selectively variable in length. Each strut may, for example, be of extensible construction with provision for locking the strut at selected lengths. The adjustability of the support portion may involve at least one strut, and preferably both struts, being adjustable in position with respect to the base portion. The adjustability of each strut with respect to the base portion may involve selective variation of the position at which the strut is attached to the base portion. Alternatively or additionally, the adjustability of each strut with respect to the base portion may involve selective variation of the angular disposition of the strut with respect to the base portion.

The adjustability of the support portion may involve the orientation of each rest member with respect to the strut on which it is supported being selectively varied. By way of example, each rest member may be mounted on the respective strut in a manner selectively permitting motion around a plurality of axes, with provision for locking the rest member in a selected position with respect to the strut.

The capacity to selectively vary the length of the struts, the position of the struts with respect to the base portion (including variation of the position at which each strut is attached to the base portion and also the angular disposition of each strut with respect to the base portion), and the orientation of the rest members with respect to the struts provides the adjustability to accommodate characteristics of the user.

The support portion may be rigid or may be adapted to yielding resist forward tilting of the head of the user beyond said predetermined point. In regard to the latter, the support portion may include a resiliently deformable section adapted to yielding resist forward tilting of the head of the patient.

The apparatus may have provision for counting or otherwise identifying the number of occurrences in which the support portion yielding resists forward tilting of the head of user during a prescribed time interval. This feature may be advantageous in circumstances where the user has an exercise or rehabilitation regimen which involves forward tilting of the head against the yielding resistance provided by the support portion, as it provides a way of identifying the number of times the action was performed. Further, the apparatus may be provided with an information transmission system for sending information on the number of occurrences of forward tilting motion to a receiver at which the information is processed and/or displayed. The receiver may be mounted on the apparatus or it may be at a remote location. By way of example, the receiver may be associated with a mobile device (such as a mobile telephone or tablet) on which there is a software application for processing and displaying the information.

In a first arrangement, the base portion is adapted to be positioned on the upper torso of the user over the shoulders of the user. In other words, the base portion is configured as a shoulder-mounted structure adapted to be positioned on the upper torso of the user.

With this arrangement, the base portion may comprise a yoke structure having two limb portions and a bridge portion extending between the two limb portions at common ends thereof. In particular, the yoke structure may be configured as an inverted U-shape. The free ends of the two limb portions define an opening through which the neck of the user can be received to allow positioning of the yoke structure on the upper torso of the user, with the bridge portion extending behind the neck of the user and the two limb portions resting on, and extending forwardly from, the shoulders of the user.

The two limb portions and the bridge portion may be of unitary construction or may be formed of sections detachably connected together.

The yoke structure may be formed of light-weight material, such as a plastics material, a light-weight metal such as aluminium, or a combination of such materials.

The yoke structure may be rigid or may be adjustable to allow the opening between the two limb portions to be selectively expanded to facilitate positioning of the yoke structure around the neck of the user. The yoke structure may be so adjustable in any appropriate way, such as by being of a resiliently deformable construction; for example, the yoke structure may comprise an elongate member formed of resiliently deformable material in a U-shape configuration.

The struts may be mounted on the two limb portions of the yoke structure. In particular, each strut may be adjustably mounted on a respective one of the two limb portions. The adjustable mounting of each strut on the respective limb portion of the yoke structure may allow selective displacement of the strut along the limb portion for varying the position at which the strut is attached to the limb portion. Additionally, the adjustable mounting of each strut on the respective limb portion of the yoke structure may allow angular movement of the strut about the limb portion for varying the angular disposition of the strut. With this arrangement, each limb portion may provide a rail around which the strut is selectively moveable angularly and/or along which the strut is selectively slidable.

The apparatus may further comprise a mounting portion configured for engagement with the rail in a manner permitting selective movement of the strut with respect to the rail.

The apparatus may further comprise a locking mechanism for releasably locking the mounting portion in a selected position with respect to the rail In one embodiment, the mounting portion may be incorporated in the respective strut and configured for engagement with the rail in a manner permitting movement with respect to the rail and a locking mechanism for locking the mounting portion in a selected position with respect to the rail. In such an embodiment, the mounting portion and the locking mechanism may be incorporated into a clamping collar having a release condition in which is can rotate about the rail and slide along the rail, and a locking condition in which is clamped to the rail and thereby restrained against rotating and sliding movement.

In another embodiment, the mounting portion is integrated with the respective strut. The locking mechanism may also integrated with the respective strut The apparatus may be of collapsible construction to provide a compact arrangement for transportation and storage. In particular, the struts may be selectively rotatable into a collapsed condition in which they are folded inwardly towards the base portion to rest upon or closely adjacent the base portion.

The support portion may detachable from the base portion. More particularly, in the arrangement involving the yoke structure, the struts may be detachable from the yoke structure.

The yoke structure itself may comprise sections adapted to be detachably connected together.

The base portion may further comprise a contact section associated with each limb portion of the yoke structure for engaging the body of a user. The contact section may be associated with the respective strut. The contact section may comprise a contact pad disposed on the underside of the respective strut.

In another arrangement, the base portion may be configured as a harness adapted to be worn by the user. The harness may be adapted to be worn on the upper torso of the user. The harness may be adjustable to accommodate the anatomy of the user, particularly the size and shape of the upper torso.

In yet another arrangement, the base portion may be configured as a sling structure adapted to be worn over one shoulder of the user.

The neck support apparatus may incorporate cushioning for comfort of the user when fitted with the neck support apparatus. In particular, various parts of the base portion and/or the support portion may be padded, encased, or otherwise fitted with cushioning material to enhance the comfort of the user. By way of example, the yoke structure may be provided with cushioning on the bridge portion where it is contacting the back of the neck and the front end of the limb portions where they will be contacting the collar bones/clavicles.

The neck support apparatus may also be equipped with ancillary devices and apparatus for various purposes, including enhancing the user experience. By way of example, the neck support apparatus may be equipped with headphone system and/or a microphone.

According to a second aspect of the invention there is provided a support apparatus comprising a base portion for positioning on a part of the body of a user, and a support portion extending from the base portion and adapted to engage a further part of the body of the user, whereby the base portion and the support portion are adapted to co-operate to afford support for the head of the user, wherein the support portion comprises a rest upon which the head of the user can be supported and two struts upon which the rest is mounted.

The support apparatus may be operable to support for the head of the user by resisting forward tilting of the head of the user beyond a predetermined point, to thereby afford support for the neck of the user. With this arrangement, the support apparatus can afford posture support to a user.

BRIEF DESCRIPTION OF THE DRAWINGS

Further features of the present invention are more fully described in the following description of several non-limiting embodiments thereof. This description is included solely for the purposes of exemplifying the present invention. It should not be understood as a restriction on the broad summary, disclosure or description of the invention as set out above. The description will be made with reference to the accompanying drawings in which.

In the drawings like structures are referred to by like numerals throughout the several views. The drawings shown are not necessarily to scale, with emphasis instead generally being placed upon illustrating the principles of the present invention.

DESCRIPTION OF EMBODIMENTS

Figure 1:
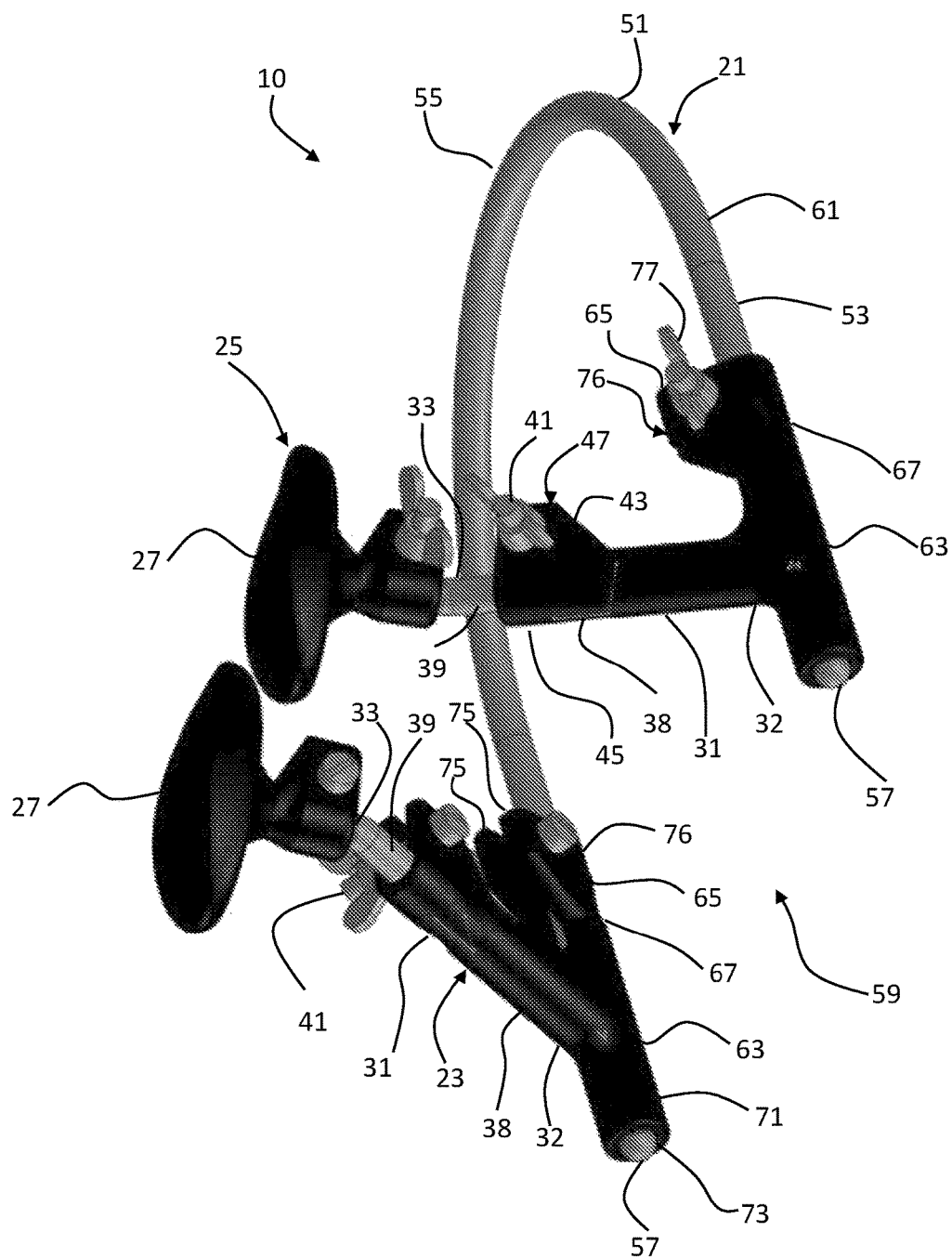
FIG. 1 is perspective view of a first embodiment of a neck support apparatus according to the invention, with the apparatus shown in an assembled condition.
Figure 2:
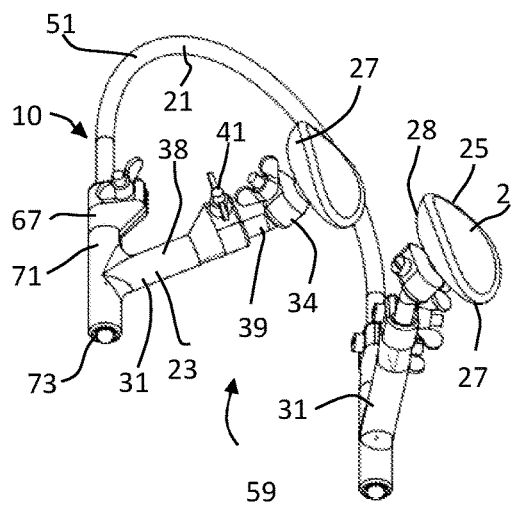
FIG. 2 is further perspective view of the neck support apparatus shown in FIG. 1.
Figure 3:
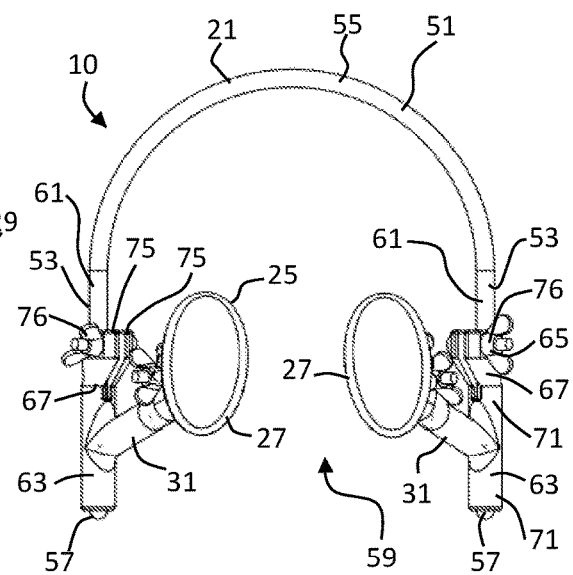
FIG. 3 is a plan view of the neck support apparatus shown in FIG. 1.
Figure 4:
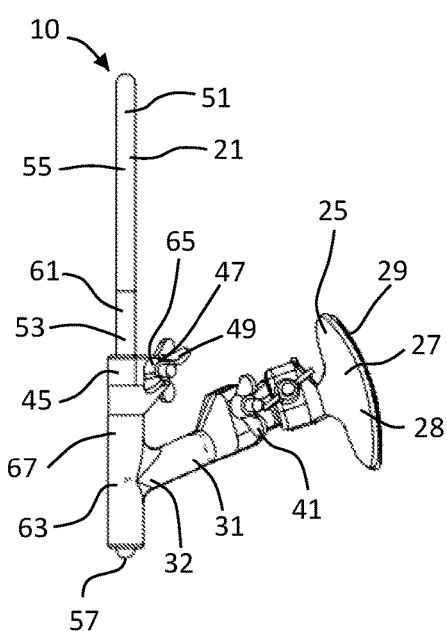
FIG. 4 is a side view of the neck support apparatus shown in FIG. 1.
Figure 5:
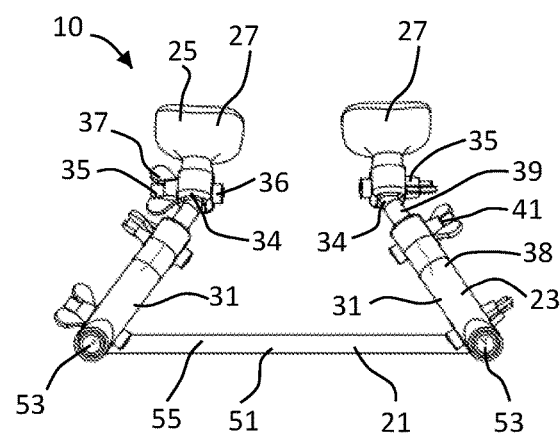
FIG. 5 is a front view of the neck support apparatus shown in FIG. 1.

Referring to FIGS. 1 to 12, there is shown a first embodiment of a neck support apparatus 10 according to the invention. The neck support apparatus 10 is described and illustrated in some drawings as being fitted onto a user 11. The user 11 is depicted with various anatomical features; namely, head 13, neck 14, shoulders 15, chin 16, mandible 17, upper torso 18 and chest 19.

Figure 7:
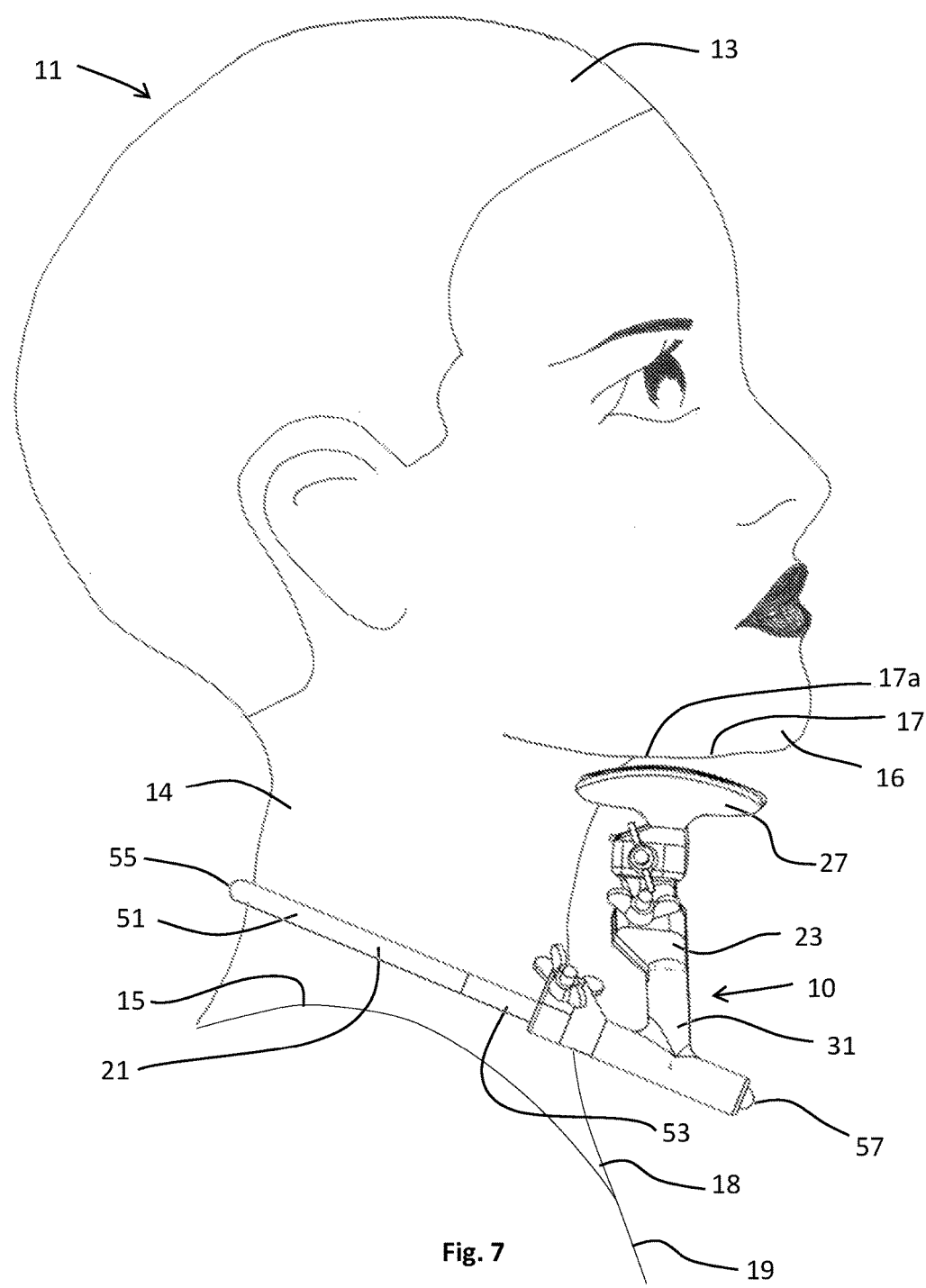
FIG. 7 is a schematic side view of the neck support apparatus shown in FIG. 1 fitted onto a user, with the head of the user being shown in a normal (unassisted) upright condition.
Figure 8:
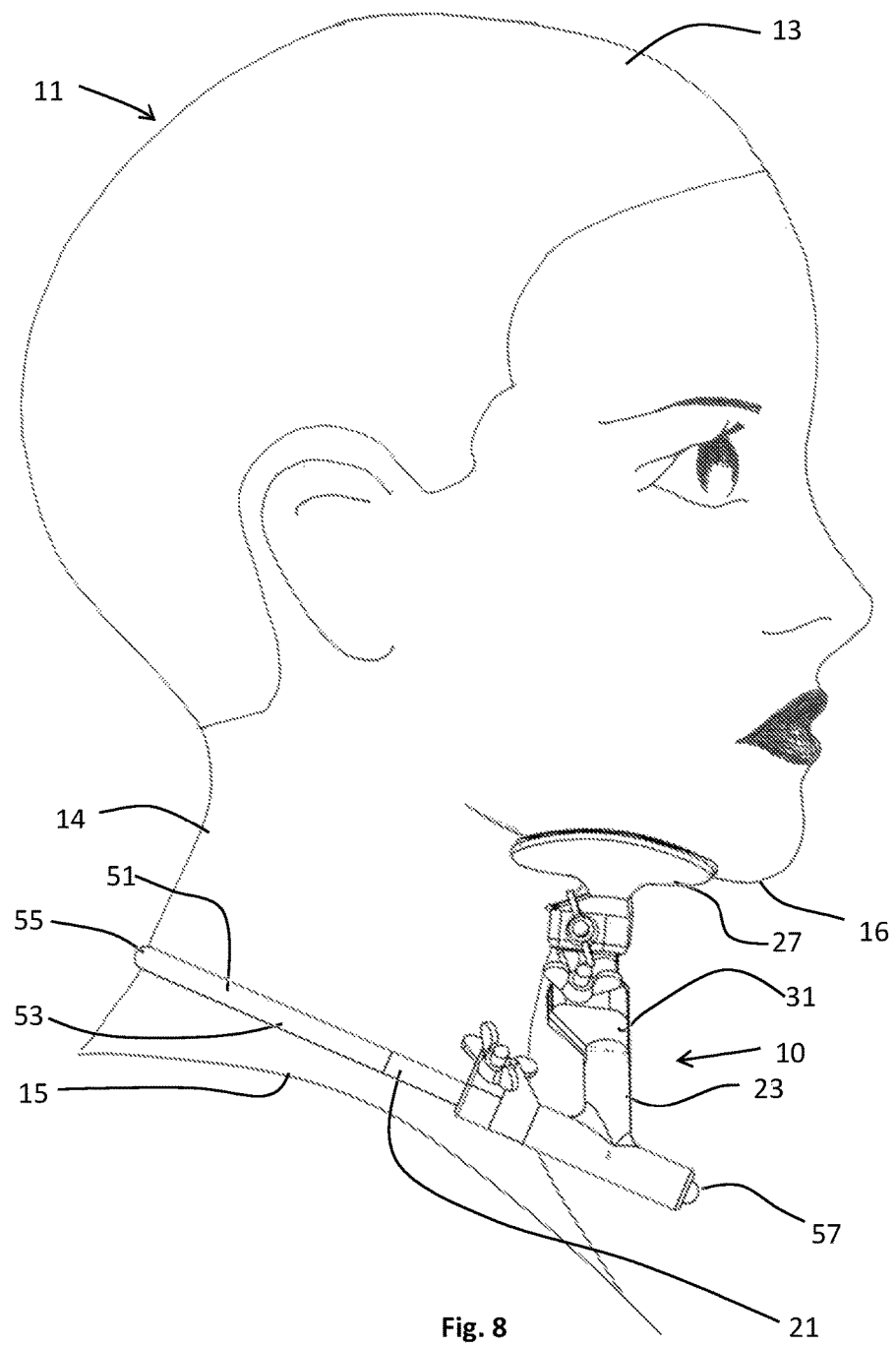
FIG. 8 is a schematic side view of the neck support apparatus shown in FIG. 1 fitted onto a user, with the head of the user being shown in a forwardly tilted condition whereby the neck support apparatus affords support for the neck of the user and resists further forward tilting of the head.
Figure 9:
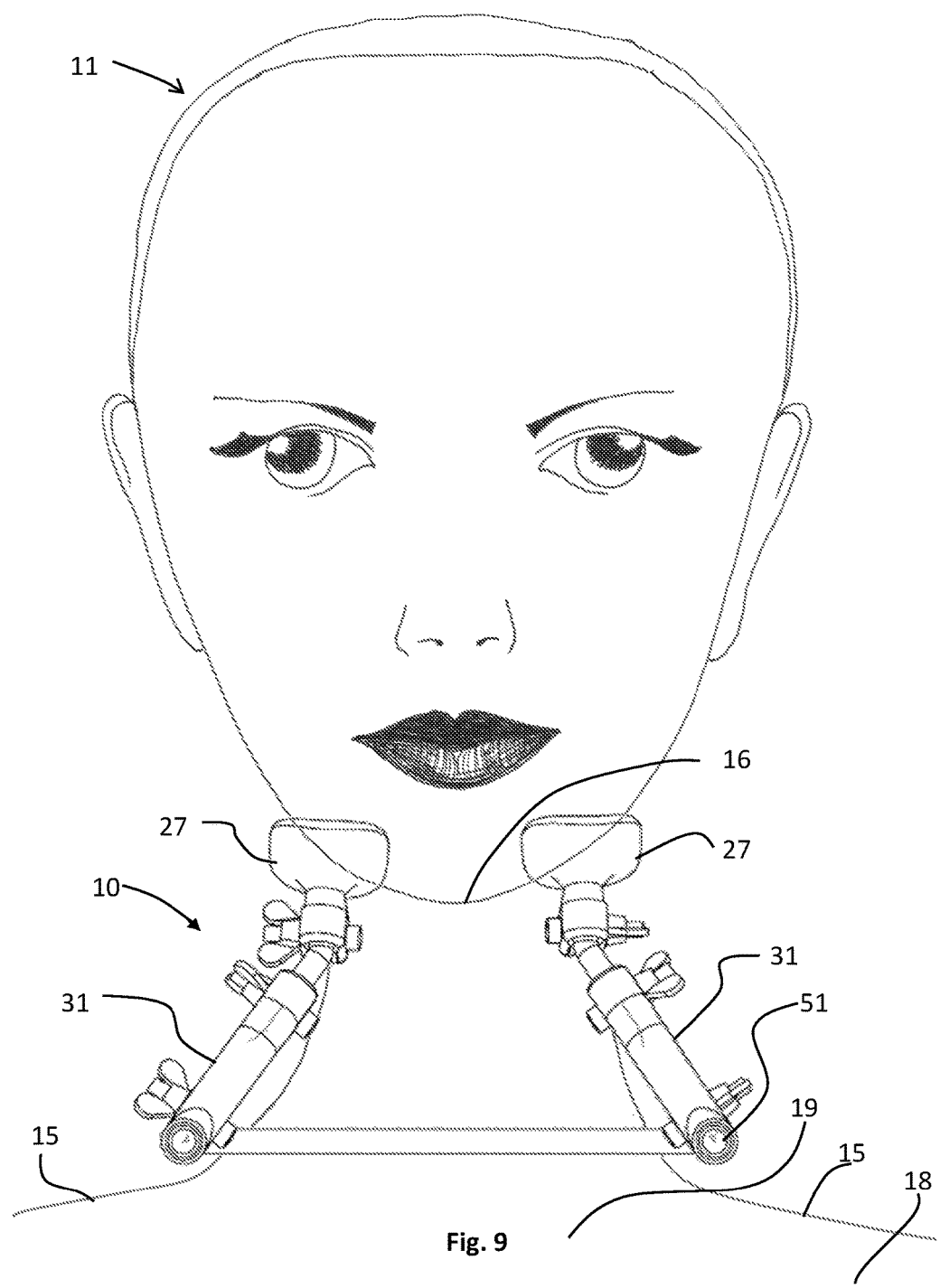
FIG. 9 is a front view of the arrangement shown in FIG. 8.
Figure 10:
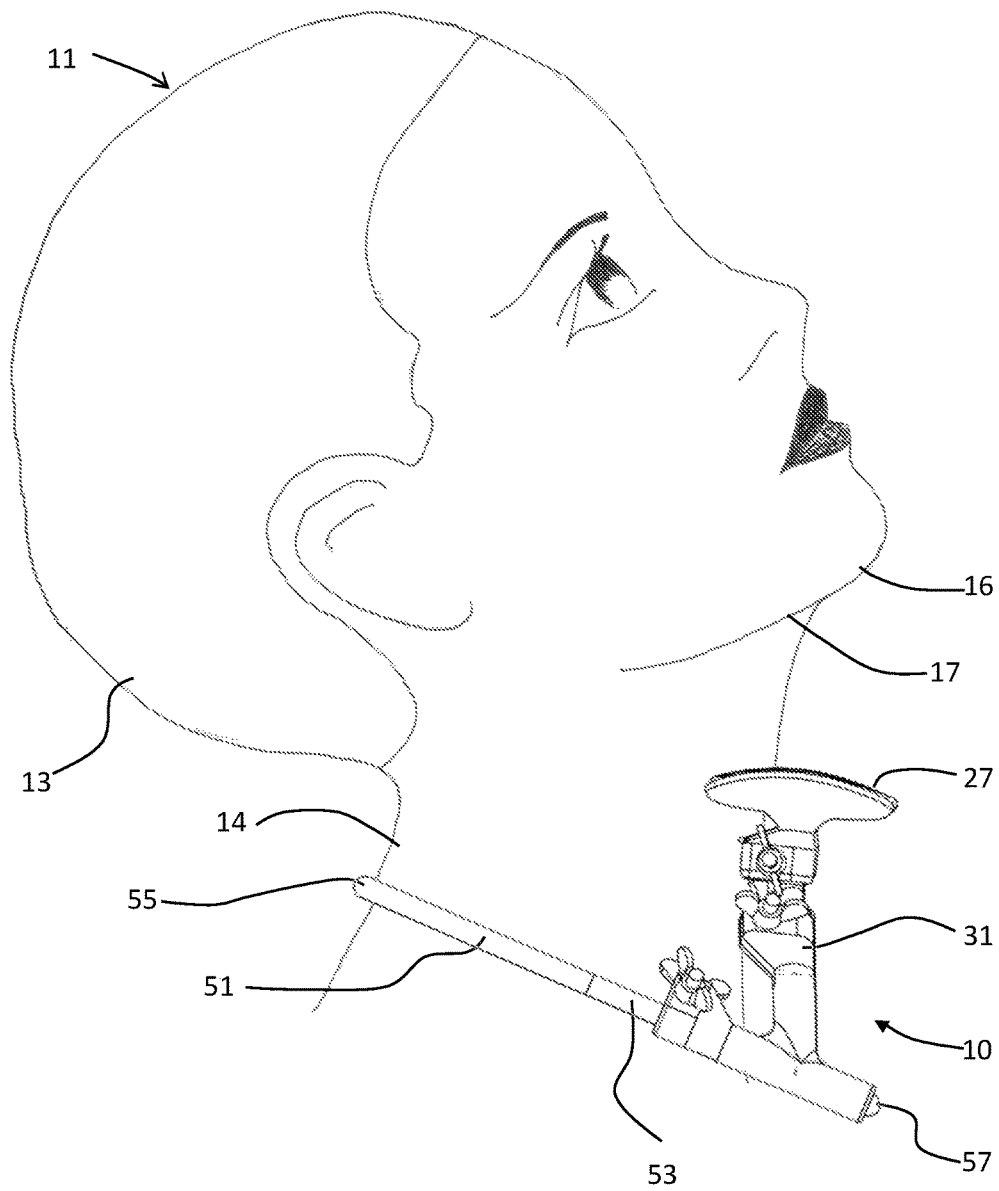
FIG. 10 is a schematic side view of the neck support apparatus shown in FIG. 1 fitted onto a user, with the head of the user being shown in a rearwardly titled condition in which there is backward extension of the neck.
Figure 11:
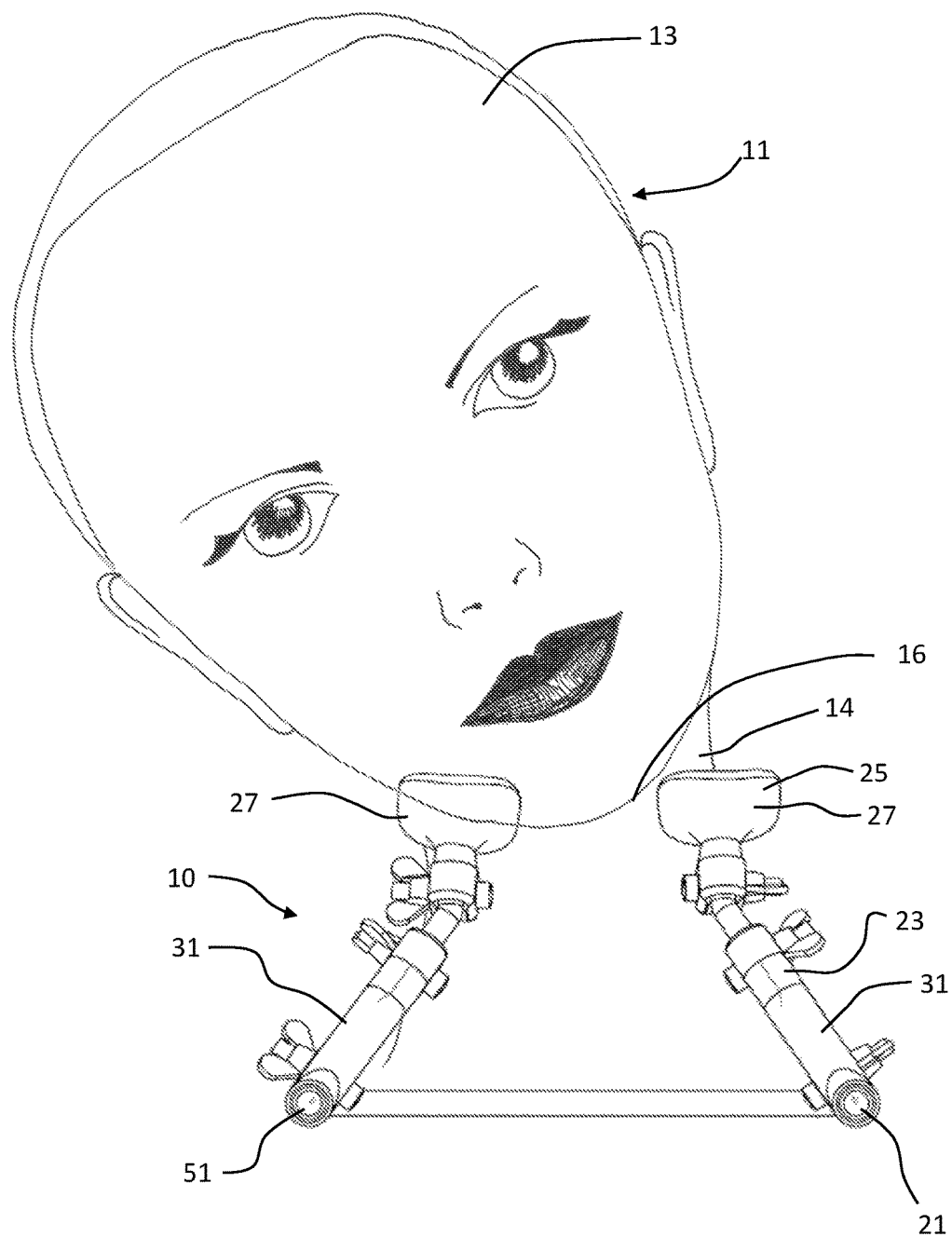
FIG. 11 is a schematic front view of the neck support apparatus shown in FIG. 1 fitted onto a user, with the head of the user being shown undergoing lateral flexion to one side.
Figure 12:
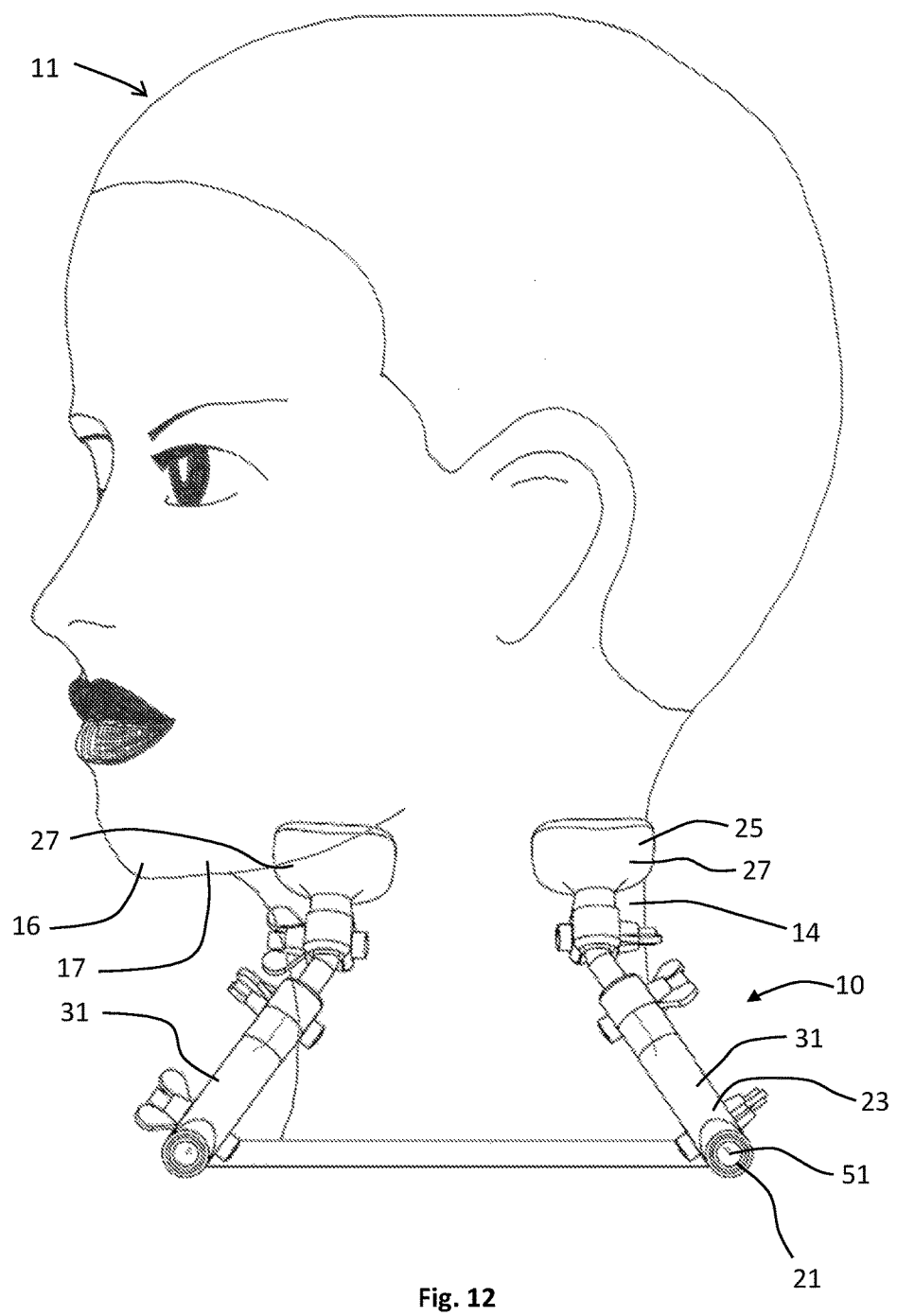
FIG. 12 is a schematic side view of the neck support apparatus shown in FIG. 1 fitted onto a user, with the head of the user being shown undergoing cervical rotation to one side.

When so fitted, the neck support apparatus 10 allows freedom of movement of the head 13 of the user 11, other than limiting forward flexion by resisting forward tilting of the head beyond a predetermined point as illustrated in FIGS. 8 and 9. The neck support apparatus 10 allows the user to assume a normal upright condition, as illustrated in FIG. 7. In the forwardmost tilted position of the head 13 of the user 11, the head of the user rests on the apparatus 10 and the apparatus 10 thereby affords support for the neck 14 of the user. More particularly, the mandible 17 of the user 11 rests on the apparatus 10. In other words, the apparatus 10 supports the neck 14 of the user 11 and also limits forward tilting of the head 13, thereby inhibiting forward flexion to an extent which would be undesirable having regard to the condition of the user. Other than resisting forward tilting of the head beyond a predetermined point, as illustrated in FIGS. 8 and 9, the neck support apparatus 10 allows freedom of movement of the head 13 of the user. In particular, the neck support apparatus 10 allows backward extension of the neck 14, as illustrated in FIG. 10. Additionally, the neck support apparatus 10 allows bilateral flexion of the neck 14, with an example of lateral flexion to one side being illustrated in FIG. 11. Additionally, the neck support apparatus 10 allows cervical rotation, with an example of cervical rotation to one side being illustrated in FIG. 12. In other words, neck support apparatus 10 allows freedom of movement of the head 13 of the user 11, other than limiting forward flexion.

In the arrangement shown in FIG. 7, the mandible 17 of the user 11 does not rest on the apparatus 10 when the head 13 is in the normal upright condition. In this way, the apparatus 10 freely allows some limited forward tilting movement of the head before commencing to support the neck 14 and limit further forward tilting of the head 13. In a variation to such an arrangement, the apparatus 10 can be configured such that the mandible 17 of the user 11 rests on the apparatus 10 when the head is in the normal condition, thereby resisting any forward tilting movement of the head beyond the normal upright condition.

The neck support apparatus 10 comprises a base portion 21 for positioning on a part of the body of the user 11 and a support portion 23 extending from the base portion and adapted to engage a further part of the body of the user, whereby the base portion and the support portion co-operate to resist forward tilting of the head 13 of the user 11 beyond a predetermined point to thereby afford support for the neck 14 of the user. In the arrangement illustrated, the further part of the body of the user 11 comprises the mandible 17, more particularly the underside of the posterior mandibles 17a.

With this arrangement, the support portion 23 comprises a rest 25 upon which the underside of the posterior mandibles 17a of the user 11 can rest when the head 13 of the user is at the forwardmost tilted position.

In this embodiment, the rest 25 is configured to receive head 13 of the user 11, typically adjacent the underside of the posterior mandibles 17a. In the arrangement illustrated, the rest 25 comprises two rest members 27 upon and between which the underside of the posterior mandibles 17a of the user 11 can rest, as illustrated in FIGS. 8 and 9.

Each rest member 27 comprises a base section 28 and a padded support section 29 which presents a surface upon which the underside of the posterior mandibles 17a of the user can rest. The padded section 28 is intended to increase comfort at the point of contact with the mandible. In another arrangement, the rest member 27 may be encased by a soft or deformable material at the point of contact with the mandible.

The support portion 23 further comprises two struts 31 which are mounted on the base portion 21 and on which the rest members 27 are mounted. More particularly, each strut 31 has an inner end section 32 adapted for connection to the base portion 21 and an outer end section 33 adapted for connection to the respective rest member 27.

Each rest member 27 is mounted on the outer end section 33 of the respective strut 31 in a manner selectively permitting motion around a plurality of axes, with provision for locking the rest member in a selected position with respect to the strut. In this way, the rest member 27 can be adjusted to register with the chin 16 of the user 11 to provide support therefor as required. In the arrangement illustrated, the rest member 27 is coupled to the outer end section 33 of the respective strut 31 through a ball and socket joint 34 which facilitates angular adjustment involving motion around a plurality of axes. The ball and socket joint 34 incorporates a locking mechanism 35 for locking the ball and socket joint 34 to retain the rest member 27 in a selected angular position. In the arrangement illustrated, the locking mechanism 35 comprises a clamping bolt assembly 36 having a nut 37 configured as a wing nut for manually tightening and loosening the clamping bolt assembly; however, other arrangements are possible.

Each strut 31 is selectively variable in length, with provision for locking the strut at selected lengths. In the arrangement illustrated, each strut 31 comprises an inner strut section 38 and an outer strut section 39 in telescopic relation, and a locking mechanism 41 for locking the two strut sections with respect to each other in a selected position. In the arrangement illustrated, the locking mechanism 41 comprises an end portion 43 of the inner strut section 38 configured as a clamping collar 45, and a clamping bolt assembly 47 for actuating the clamping collar. The clamping bolt assembly 47 has a clamping nut 49 configured as a wing nut for manually tightening and loosening the clamping bolt assembly; however, other arrangements are possible.

The base portion 21 is adapted to be positioned on the upper torso 18 of the user 11 over the shoulders 15 of the user 11. In other words, the base portion 21 is configured as a shoulder-mounted structure adapted to be positioned on the upper torso 18 of the user 11.

In this embodiment, the base portion 21 is configured as a yoke structure 51 having two limb portions 53 and a bridge portion 55 extending between the two limb portions at common ends thereof. In the arrangement illustrated, the yoke structure 51 is configured as an inverted U-shape. The free ends 57 of the two limb portions 53 define an opening 59 through which the neck 14 of the user 11 can be received to allow positioning of the yoke structure 51 on the upper torso 18 of the user 11, with the bridge portion 55 extending behind the neck 14 and the two limb portions 53 resting on, and extending forwardwards from, the shoulders 15 in front of the upper torso 18 of the user, as best seen in FIGS. 7, 8 and 9.

The two limb portions 53 and the bridge portion 55 are of unitary construction in this embodiment. Other arrangements are possible; for example, two limb portions 53 and the bridge portion 55 may be formed of sections detachably connected together.

The yoke structure 51 may be formed of light-weight material, such as a plastics material, a light-weight metal such as aluminium, or a combination of such materials.

In this embodiment, the yoke structure 51 is a rigid arrangement such that the two limb portions 53 and the bridge portion 55 are fixed in position with respect to each other. Other arrangements are possible; for example, the yoke structure 51 may be adjustable to allow the opening 59 between the two limb portions 53 to be selectively expanded to facilitate positioning of the yoke structure around the neck 14 of the user 11. The yoke structure 51 may be so adjustable in any appropriate way, such as by being of a resiliently deformable construction; for example, the yoke structure 51 may comprise an elongate member formed of resiliently deformable material in a U-shape configuration.

The struts 31 are mounted on the two limb portions 53 of the yoke structure 51. In particular, each strut 31 is adjustably mounted on a respective one of the two limb portions 53. The adjustable mounting of each strut 31 on the respective limb portion 53 of the yoke structure 51 allows selective angular movement of the strut about the limb portion for varying the angular disposition of the strut, and also selective displacement of the strut along the limb portion for varying the position at which the strut is attached to the limb portion. With this arrangement, each limb portion 53 provides a rail 61 around which the strut 53 is selectively moveable angularly and along which the strut is selectively slidable.

In this embodiment, the inner end section 32 of each strut 31 is configured to provide a mounting portion 63 for engagement with the rail 61 in a manner permitting rotational and slidable movement with respect to the rail, and a locking mechanism 65 for locking the mounting portion 63 in a selected position with respect to the rail. In the arrangement illustrated, the mounting portion 63 and the locking mechanism 65 are incorporated a clamping collar 67 having a release condition in which is can rotate about the rail and slide along the rail 61 and a locking condition in which is clamped to the rail and thereby restrained against rotating and sliding movement. In the arrangement illustrated, the clamping collar 67 comprises a sleeve section 71 defining a bore 73 in the rail can be received. The sleeve section 71 has a section thereof which is split so that it can expand and contract radially and incorporates integral tabs 75 on opposed sides of the split. A manually operable clamping bolt assembly 76 extends between the tabs 73 for opening and closing the slit and thereby radially expanding and contracting the sleeve section 71 on the rail 61. In the arrangement illustrated, the clamping bolt assembly 76 includes a nut 77 configured as a wing nut for tightening and loosening the clamping bolt assembly; however, other arrangements are possible.

With this arrangement, the sleeve section 71 provides the mounting portion 63 at the inner end section 32 of each strut 31. Additionally, the sleeve section 71 in combination with the clamping bolt assembly 76 provides the locking mechanism 65 for locking the mounting portion 63 in a selected position with respect to the rail 61.

In this embodiment, the inner strut section 38 of each strut 31 incorporates the inner end section 32 of the strut. Additionally, the inner strut section 38 of each strut 31 incorporates both the locking mechanism 41 and the clamping collar 67.

Various parts of the base portion 21 and the support portion 23 may be padded, encased, or otherwise fitted with cushioning material to enhance the comfort of the user when fitted with the neck support apparatus 10.

The neck support apparatus 10 may also be equipped with ancillary devices and apparatus for various purposes, including enhancing the user experience. By way of example, the neck support apparatus 10 may be equipped with headphone system and/or a microphone.

Figure 6:
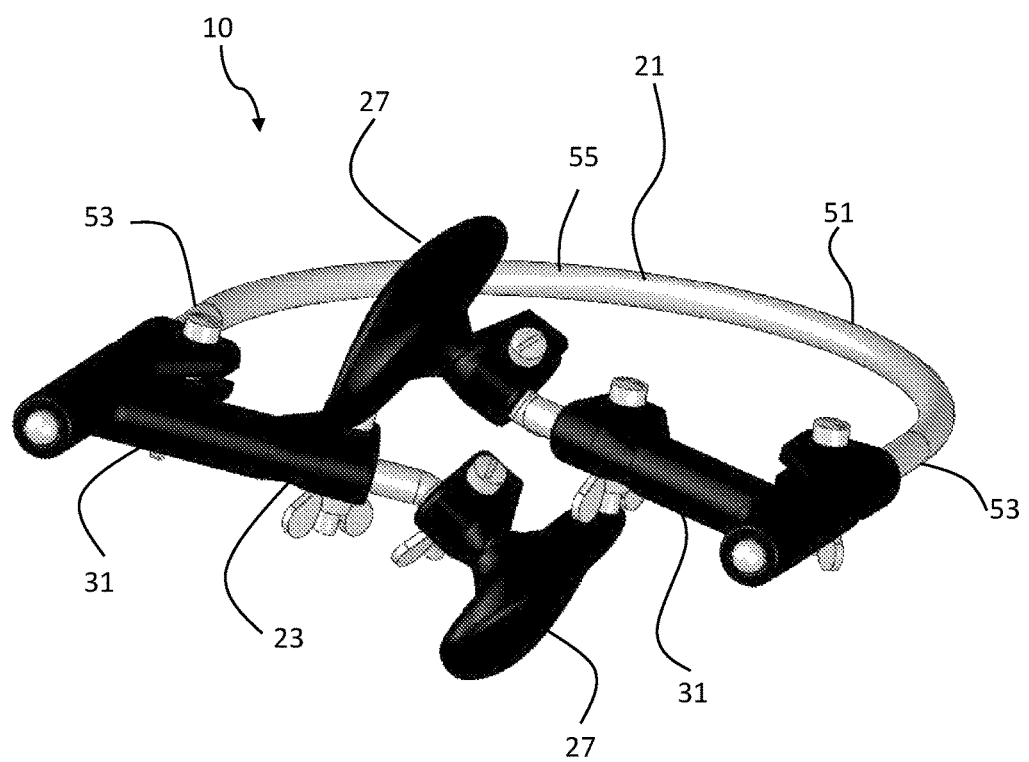
FIG. 6 is perspective view of the first embodiment of a neck support apparatus, with the apparatus shown in a collapsed condition.

By virtue of its construction, this embodiment of the apparatus 10 is selectively movable between an operative (assembled) condition as shown in FIG. 1 and a collapsed condition as shown in FIG. 6. The collapsed condition provides a compact arrangement for transportation and storage. In particular, the struts 31 may be selectively rotatable into a collapsed condition in which they are folded inwardly towards the yoke structure 51 to rest upon or closely adjacent to the yoke structure, as shown in FIG. 6.

By virtue of the construction of this embodiment of the apparatus 10, support portion 23 is detachable from the base portion 21. More particularly, the struts 31 may be detachable from the yoke structure 51. This may be advantageous for transportation and storage of the apparatus 10.

Operation of the neck support apparatus 10 will now be described. The apparatus 10 is fitted onto the user 11 by positioning the yoke structure 51 on the upper torso 18 of the user 11, with the bridge portion 55 extending behind the neck 14 and the two limb portions 53 resting on and extending forwardly from the shoulders 15 of the user, as best seen in FIGS. 7, 8 and 9. The struts 31 are then adjusted as necessary, and the rest members 27 are adjusted as necessary on the struts, to appropriately position the rest members 27 with respect to the mandible 17 of the user 11.

The two struts 31 are adapted to be disposed angularly with respect to each other, whereby in use the two struts can extend upwardly and inwardly towards the mandible 17 of the user 11, as best seen in FIG. 9. This arrangement is advantageous as it facilitates support for, and positioning of, the two rest members 27 in a manner which does not adversely obstruct the field of vision of the user 11. Furthermore, it is believed that the arrangement is not too bulky or cumbersome aesthetically to deter use of the support apparatus, With the neck support apparatus 10 fitted in position, the user 11 has freedom of movement of his or her head 13, other than limited forward flexion as previously described. In particular, the neck support apparatus 10 allows backward extension of the neck 14, as illustrated in FIG. 10. The neck support apparatus 10 also allows bilateral flexion of the neck 14, with an example of lateral flexion to one side being illustrated in FIG. 11. Additionally, the neck support apparatus 10 allows cervical rotation, with an example of cervical rotation to one side being illustrated in FIG. 12. In relation to cervical rotation, in some instances the jaw section of the user 11 may be elevated in relation to the rest members 27, allowing the adjacent posterior mandible 17*a* and the chin 16 to pass over the respective rest member 27 during turning movement of the head. In other instances, the chin 16 of the user 11 may contact the respective rest member 27 during turning movement of the head. This does not present a difficulty, as the yoke structure 51 can merely swing about the neck 14 of the user in concert with the turning head of the user.

Once the neck support apparatus 10 has been adjusted to fit the user concerned, the user can easily remove and fitted in position as necessary. In order to remove the neck support apparatus 10 once adjusted to fit in position, the user 11 simply moves the yoke structure 51 backwards and lifts it from the upper torso 18, with the yoke structure moving rearwardly away from around the neck 14. The user 11 can return the neck support apparatus 10 into position on the upper torso 18 as required by simply positioning the yoke structure 51 around the neck 14, with the latter being received through the opening 59 to allow positioning of the yoke structure 51 on the upper torso 18 of the user 11, with the bridge portion 55 extending behind the neck 14 and the two limb portions 53 extending forwardwardly from the shoulders 15.

In this way, the user is able to use the neck support apparatus 10 when there is a requirement to do so. In certain instances, a user may use the neck support apparatus 10 for extended periods, such as when there is a need for rehabilitation of a neck injury. In certain instances, a user may use the neck support apparatus 10 only when circumstances so require, such as when working at a desk or in some other situation where the user might be prone to allowing his or her head to tilt forward to an undesirable extent.

When not in use, the neck support apparatus 10 can be stored in the collapsed conditions as shown in FIG. 6.

The neck support apparatus 10 is intended for use when a user is in an upright or seated position where the head of the user is vulnerable to tilting forward. The neck support apparatus 10 is not intended for use when a user is in a sleeping position, or in a prostrate or supine position.

In the first embodiment of the neck support apparatus 10 as described and illustrated, the rest 25 is supported in a rigid manner in the sense that it was not movable in response to loading imposed upon it through the chin 16 of the user during forwarding tilting of the head 13 (apart from any incidental movement inherent in the construction of the rest, such as any flexibility in the padded support section 29 of each rest member 27).

In certain applications, it may be desirable that the rest 25 be supported in a manner adapted to yielding resist forward tilting of the head of the user beyond said predetermined point. In this regard, the support portion may include a resiliently deformable section adapted to yielding resist forward tilting of the head of the patient.

Figure 13:
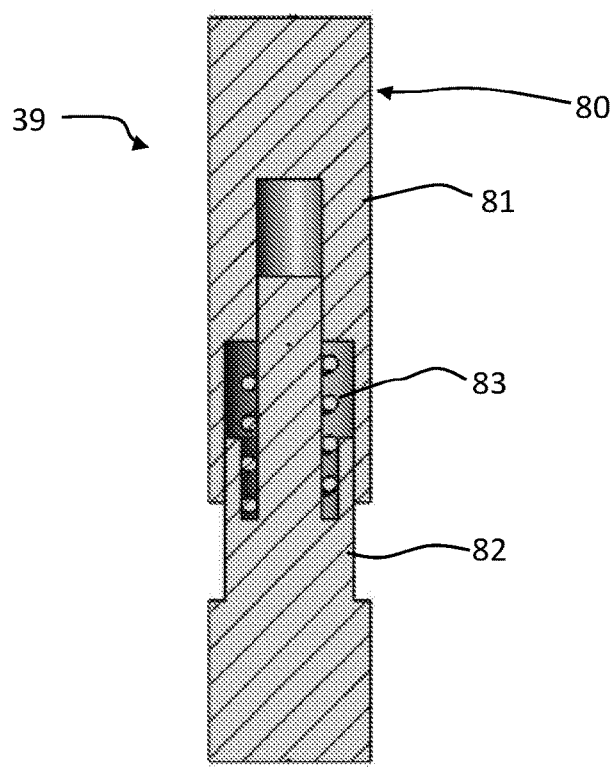
FIG. 13 is a sectional view of part of a second embodiment of a neck support apparatus according to the invention.

The second embodiment of the neck support apparatus 10, a part of which is shown in FIG. 13, incorporates such an arrangement. The second embodiment is similar in many respects to the first embodiment and corresponding reference numerals are used to identify corresponding parts.

In this second embodiment, each strut 31 is constructed to yieldingly deform in the axial direction when subjected to a loading imposed upon it through the mandible 17 of the user during forwarding tilting of the head 13 user beyond said predetermined point.

In the arrangement shown, the outer strut section 39 of each strut 31 comprises an extensible member 80 which is resiliently contactable under inward axial loading. Specifically, the extensible member 80 comprises first and second sections 81, 82 interconnected in axial sliding relation to provide a telescoping arrangement. The extensible member 80 further comprises biasing means 83 such as a compression spring operating between the first and second sections 81, 82 to urge them apart so that the extensible member 80 assumes a fully extended condition. The extensible member 80 is contractible in response to inward axial loading exceeding the opposing force exerted by the biasing means 83, with the biasing means 83 yielding progressively to allow the contraction while continually opposing the contraction.

With this arrangement, each strut 31 can yielding contract when subjected to a loading imposed upon it through the chin 16 of the user 11 during forward tilting of the head 13 user beyond said predetermined point which corresponds to the position of the rest members 27 when the extensible member 80 are in the fully extended conditions. This contraction facilitates movement of the rest member 27, accommodating and yet yieldingly resisting the movement of the forward tilting of the head 13. The user may perform an exercise or treatment regimen involving a series of forward tilting movements of the head against the resistance. The yielding resistance allows the user 11 to strengthen the muscles supporting the cervical vertebrae with active exercise.

In certain applications, it may be desirable that there be provision for counting or otherwise identifying the number of occurrences in which forward tilting of the head is yieldingly resisted over a prescribed time interval. This feature may be advantageous in circumstances where the user has an exercise or rehabilitation regimen which involves forward tilting of the head again the yielding resistance, as it provides a way of identifying the number of times the action was performed.

Figure 14:
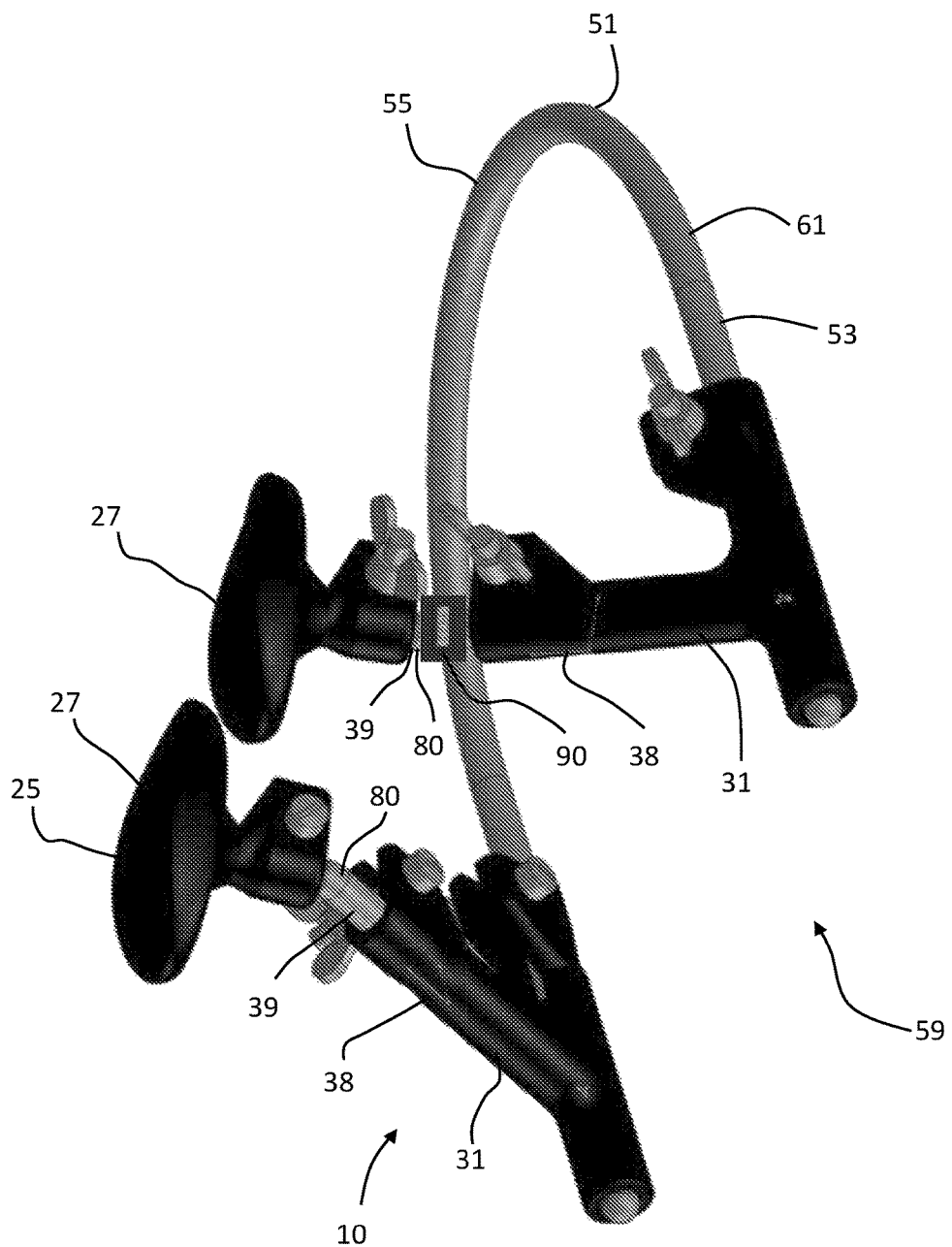
FIG. 14 is perspective view of a third embodiment of a neck support apparatus according to the invention, with the apparatus shown in an assembled condition.
Figures 15, 16:
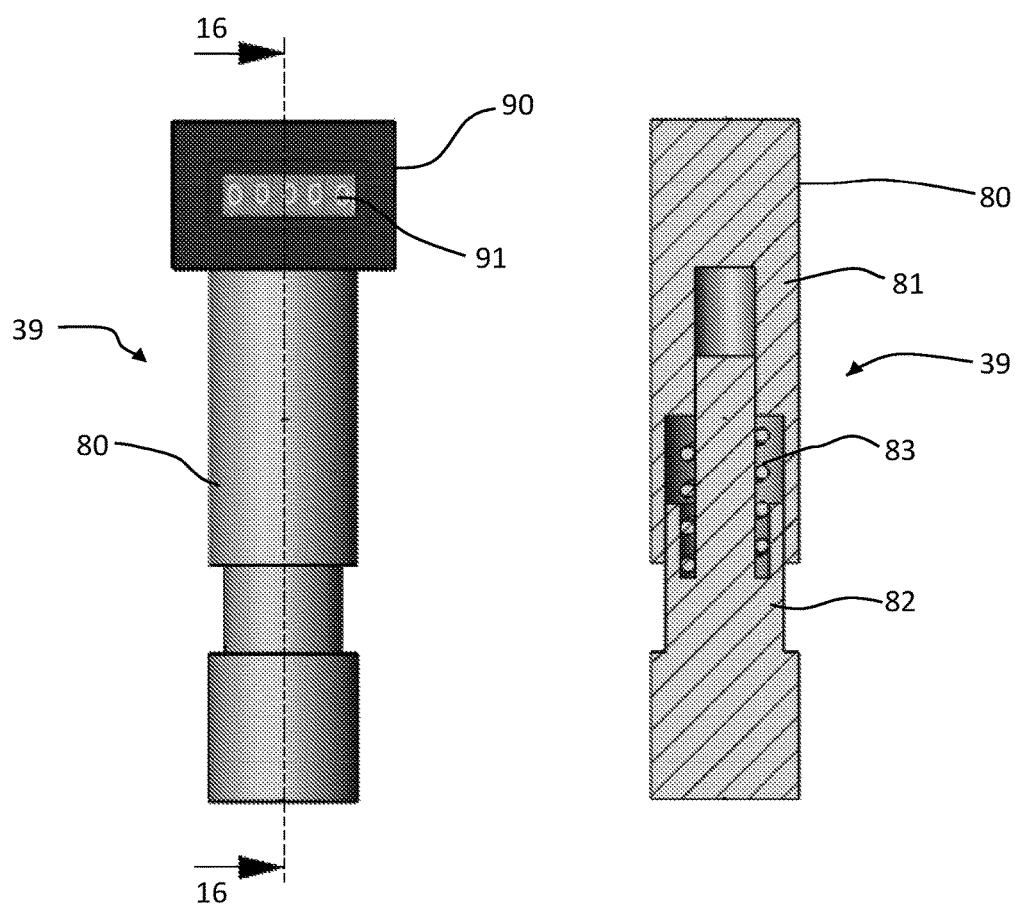
FIG. 15 is a view of part of the neck support apparatus shown in FIG. 14.
FIG. 16 is a sectional view along line 16-16 in FIG. 15.

The third embodiment of the neck support apparatus 10, which is shown in FIGS. 14, 15 and 16, incorporates such an arrangement. The third embodiment is similar in many respects to the second embodiment and corresponding reference numerals are used to identify corresponding parts.

In the third embodiment, the outer strut section 39 of each strut 31 comprises the extensible member 80 which is used in the second embodiment. One strut 31 is fitted with a counter 90 or other recording system operably connected to the extensible member 80 for recording the number of times the forward tilting action of the head again the yielding resistance was performed and displaying the accumulated information.

In the arrangement shown, the counter 90 is physically mounted on one of the struts 31 and incorporates a visual display 91. Other arrangements are possible. The counter 90 may comprise a sensor for sensing the number of contractions and a transmitter for transmitting the sensed information to a receiver at which the information is processed and/or displayed. The receiver may be mounted on the neck support apparatus 10 or it may be at a remote location. By way of example, the receiver may be associated with a mobile device (such as a mobile telephone or tablet) on which there is a software application for processing and displaying the information. Of course, any other appropriate form of information transmission system may be provided for sending information on the number of occurrences of forward tilting motion.

Figure 17:
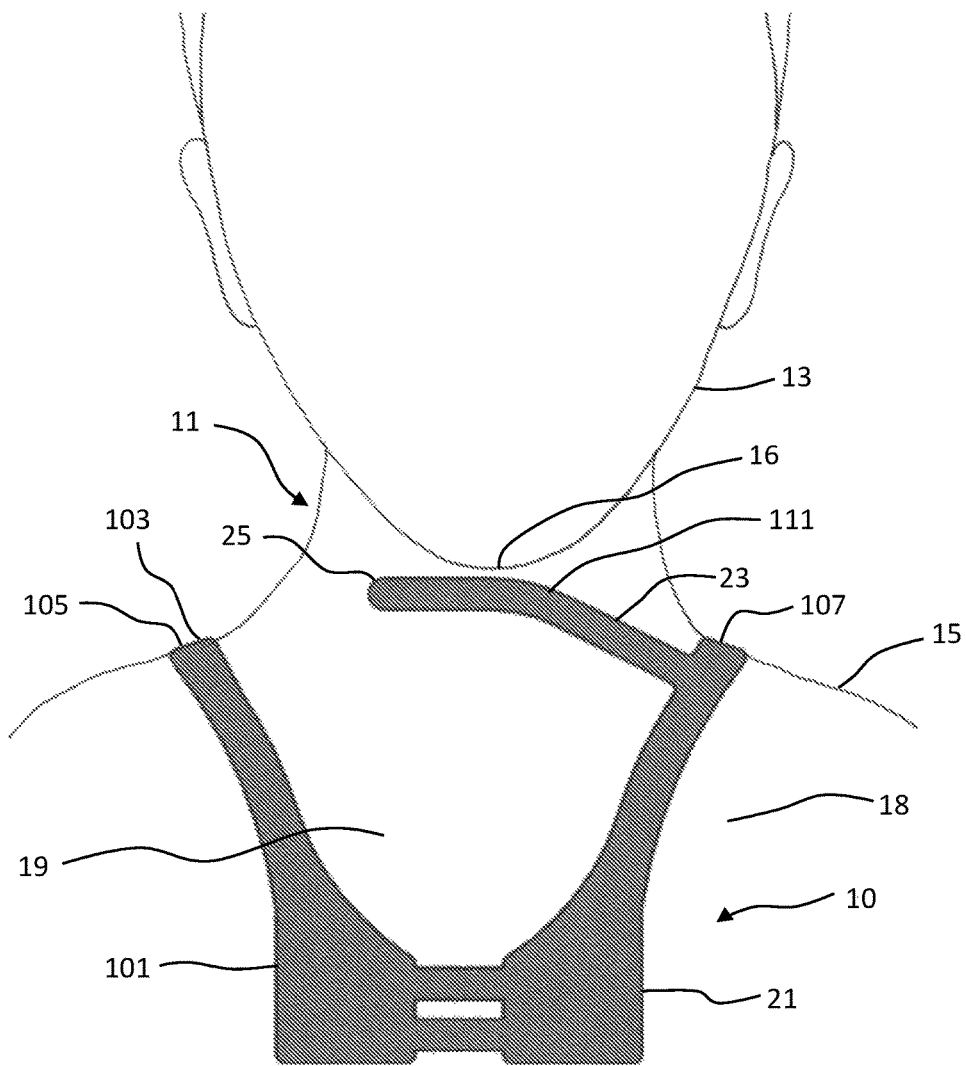
FIG. 17 is a schematic front view of a fourth embodiment of a neck support apparatus according to the invention, with the apparatus shown fitted onto a user.
Figure 18:
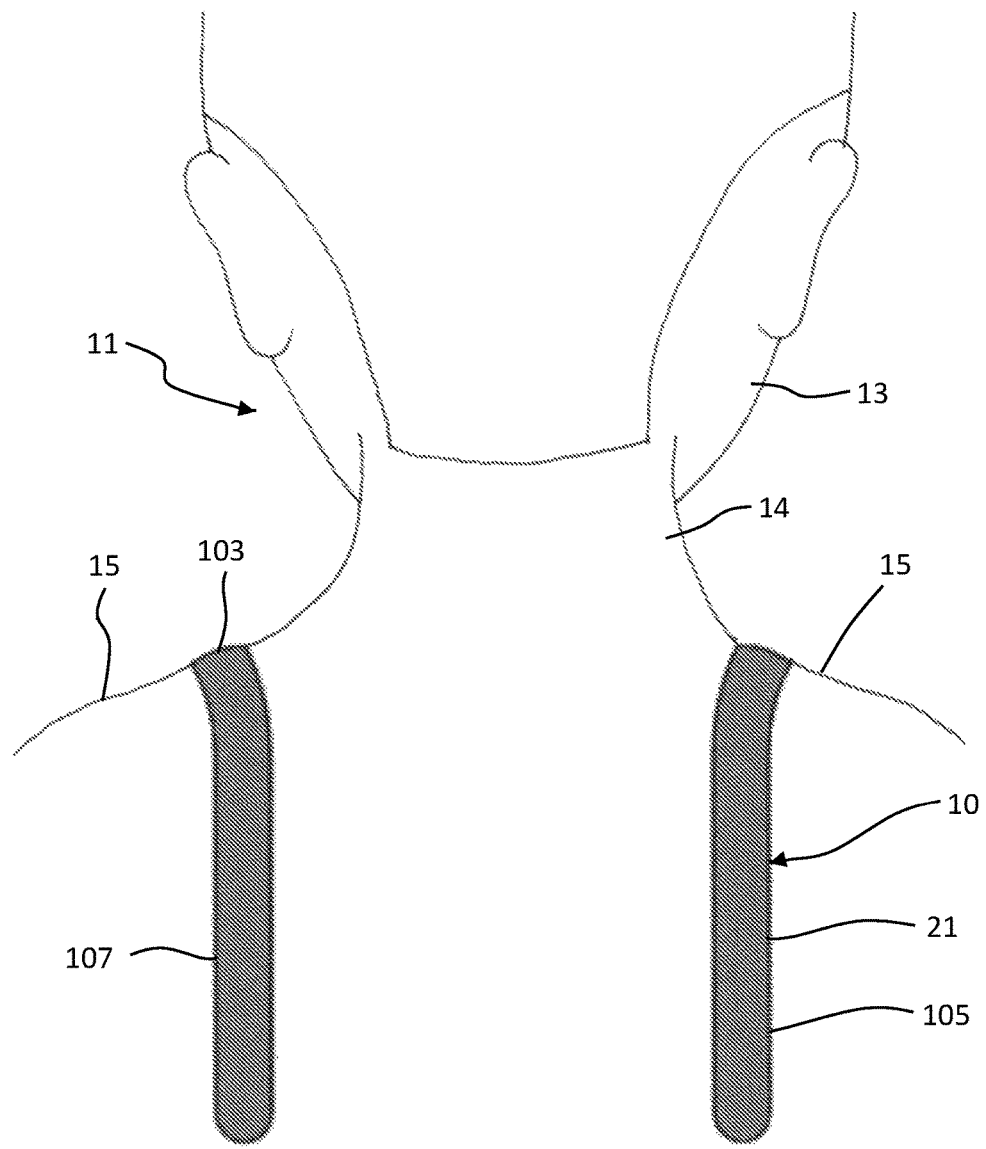
FIG. 18 is a rear view of the arrangement shown in FIG. 17.
Figure 19:
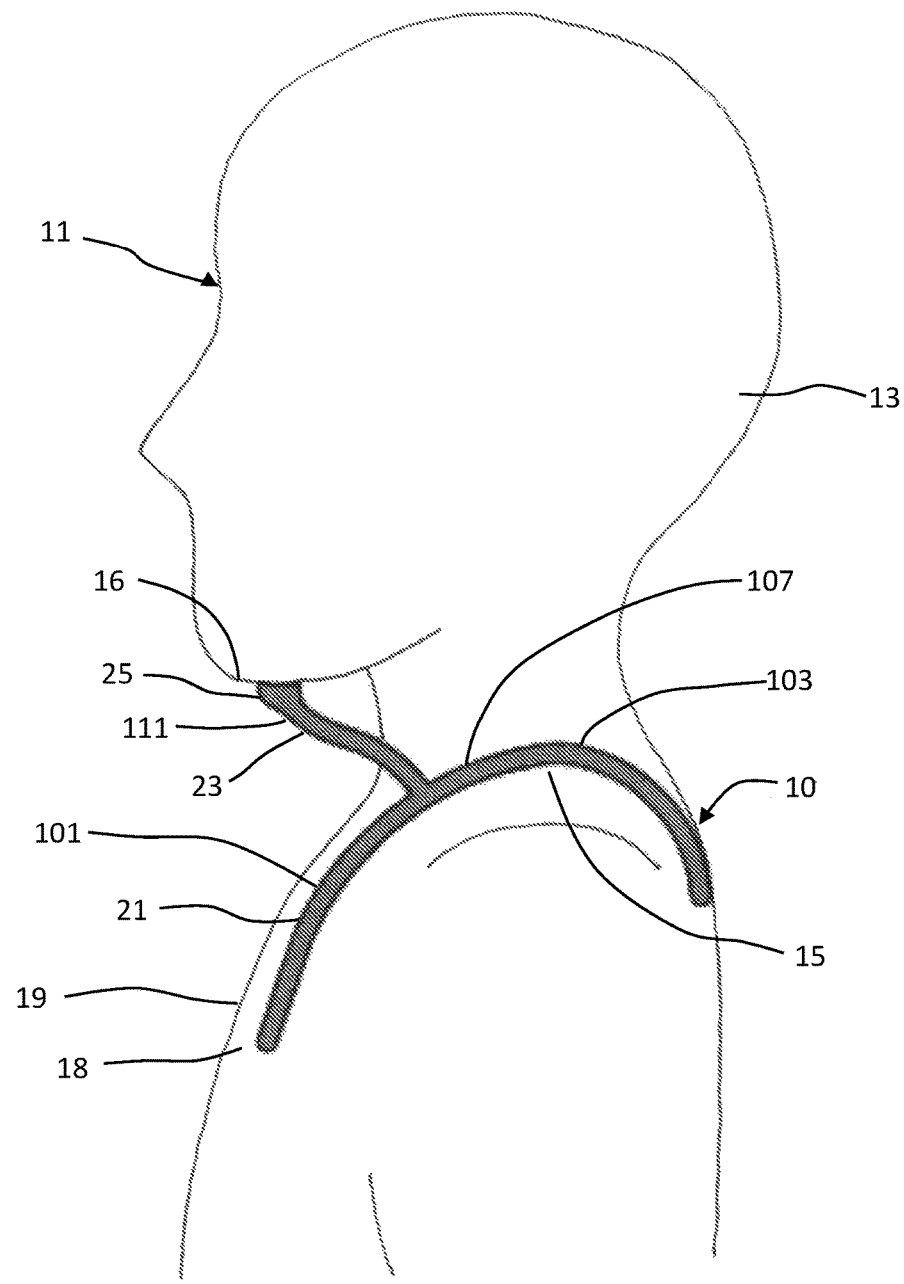
FIG. 19 is a side view of the arrangement shown in FIG. 17.

Referring now to FIGS. 17, 18 and 19, there is shown a fourth embodiment of a neck support apparatus 10 according to the invention. The fourth embodiment is similar in some respects to the first embodiment and corresponding reference numerals are used to identify corresponding parts where appropriate.

The fourth embodiment of the neck support apparatus 10 is configured as a base portion 21, wearable on a user's upper torso 18, and an integrally mounted support portion 23, adapted to engage and support the user's chin 16 and thereby offer neck support.

The base portion 21 and the support portion 23 of the neck support apparatus 10 are of integral construction and comprise a plastics material.

The base portion 21 comprises a chest plate 101 which is in contact with a user's chest 19, and a shoulder support 103 configured as two hooked members 105 and 107 which are integrally connected to the chest plate 101. The hooked members 105 and 106 extend above the front, around the top and down the back of a user's shoulders 15, to anchor the neck support apparatus 10 to the upper torso 18.

The support portion 23 comprises a projection 111 which is integrally attached to the base portion 21 on the upper front section of one of the hooked members 105 or 107. The projection 111 is configured as a strut in the form of a cantilever which projects upwardly and inwardly towards the underside of a user's chin 16. The end of the projection 111 incorporates the rest 25. In the arrangement shown, the free end section of the projection 111 is configured to have a large profiled contact area for receiving the underside of the user's chin 16, thereby defining the rest 25. The projection 111 is positioned to make contact with the chin 16 when the user's head is in an upright position or tilted forwarded slightly to an extent deemed acceptable. The projection 111 is resiliently flexible. This feature is achieved through the configuration of the projection 111 and the characteristics of the plastics material from which it is formed.

In a variation, the present arrangement may only use one hooked member 105 or 107 for anchoring the neck support apparatus 10 to the upper torso 18.

As the user 11 tilts his or her head forwards, the support portion 23 yielding resists the forward tilting of the patient's head. The yielding resistance is achieved by the deforming of the projection 111 through resilient flexion under the force exerted upon it by the user's chin 16. Once the force exerted upon the projection 111 ceases, the projection will revert to its original form and position. The yielding resistance allows the user to strengthen the muscles supporting the cervical vertebrae with active exercise.

Figure 20:
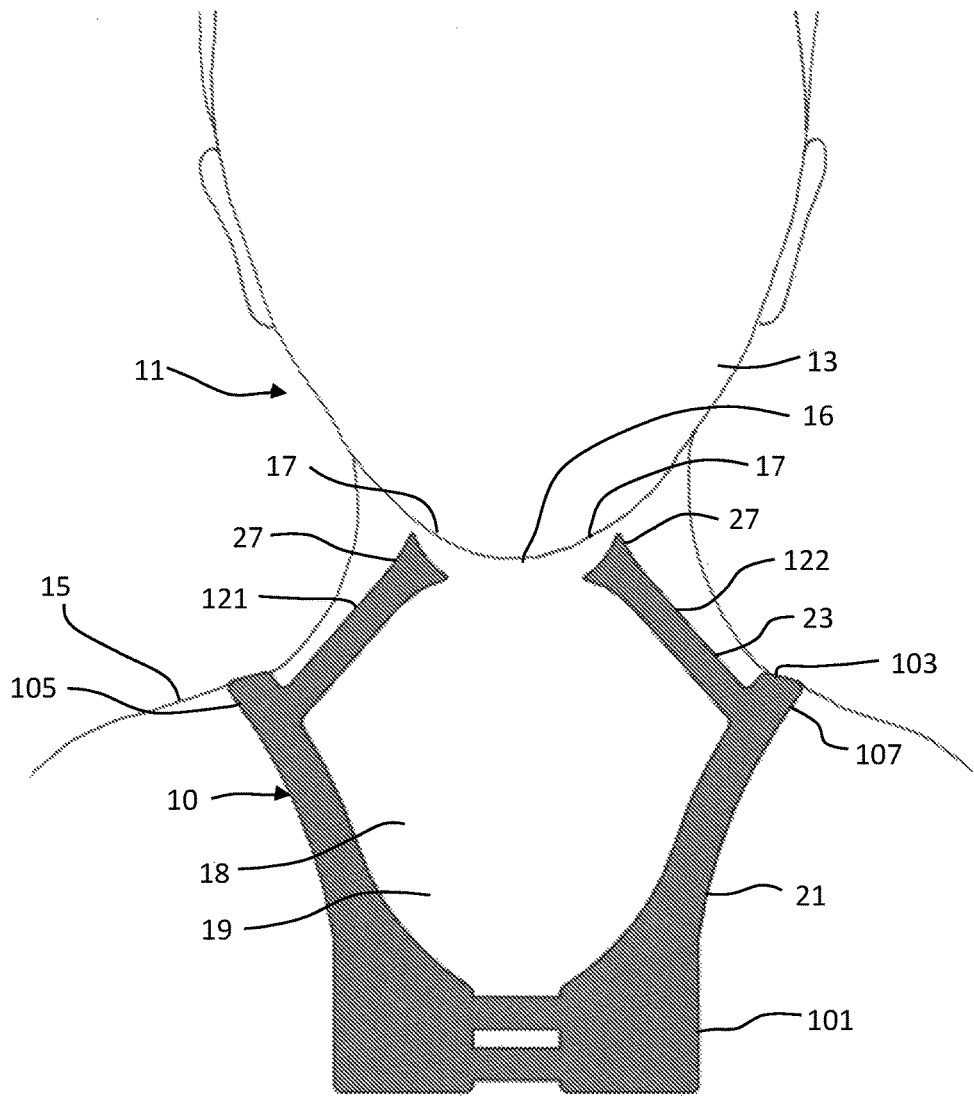
FIG. 20 is a schematic front view of a fifth embodiment of a neck support apparatus according to the invention, with the apparatus shown fitted onto a user.
Figure 21:
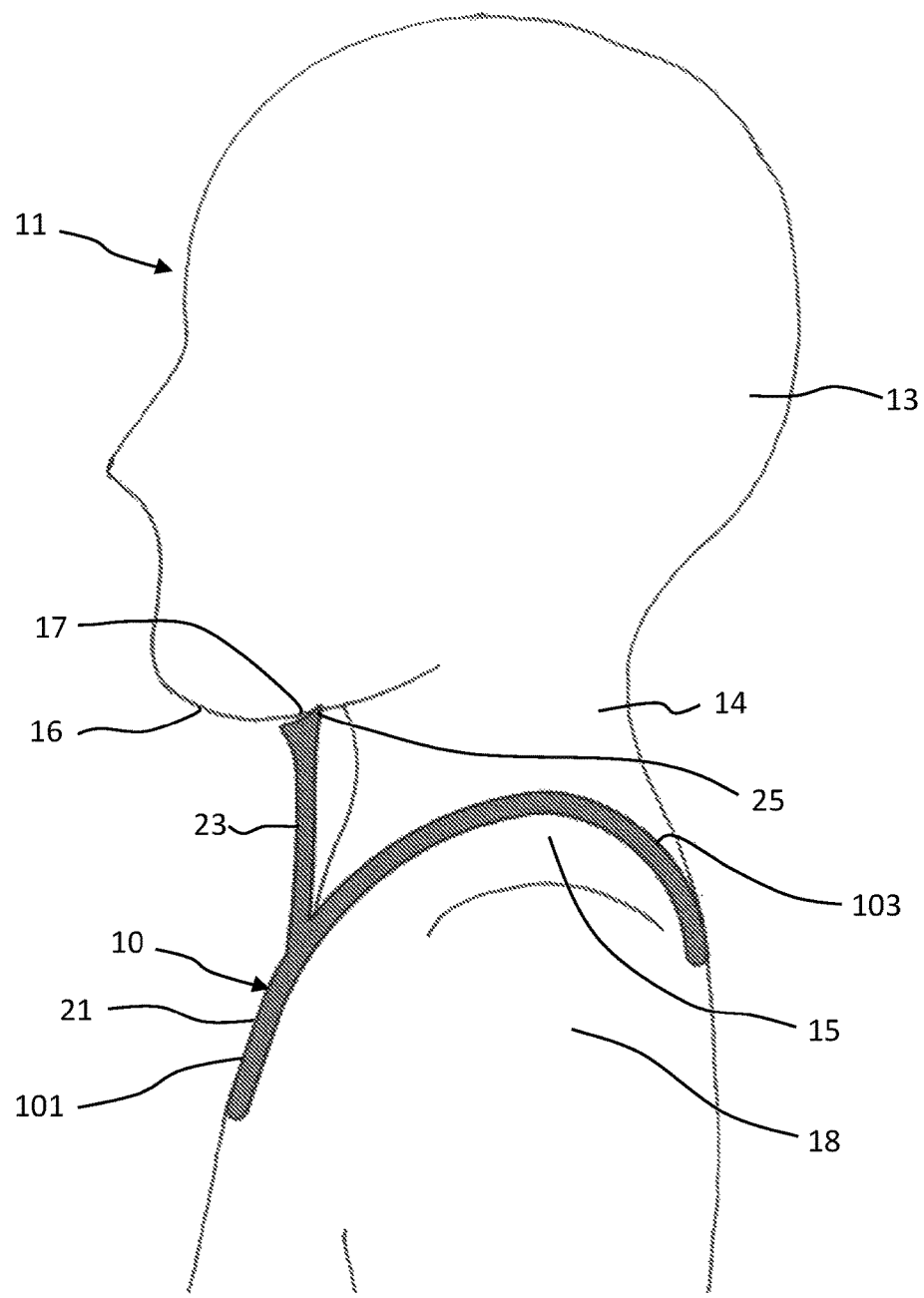
FIG. 21 is a side view of the arrangement shown in FIG. 20.

Referring now to FIG. 20 and, there is shown a fifth embodiment of a neck support apparatus 10 according to the invention. The fifth embodiment is similar in some respects to the fourth embodiment and corresponding reference numerals are used to identify corresponding parts where appropriate.

The neck support apparatus 10 is configured as a base portion 21 mountable on a user's upper torso 18, and a support portion 23 adapted to engage and support chin 16 adjacent the posterior mandibles 17 and thereby offer neck support. In this embodiment, the support portion 23 comprises two support members 121 and 122, each configured as a strut providing a projection extending upwardly and inwardly.

The base portion 21 and the support portion 23 of the neck support 10 apparatus are of integral construction and comprise plastics material.

The base portion 21 comprises chest plate 101 which is in contact with a user's chest 19, and shoulder support 103 configured as hooked members 105 and 107 which are integrally connected to the chest plate. The hooked members 105 and 107 extend above the front, around the top and down the back of a user's shoulders 15, to anchor the neck support apparatus 10 to the upper torso 18.

The two support members 121 and 122 are integrally attached to the base portion 21, with each support member attached to a separate upper front section of the hooked members 105 and 107. This ensures that there is even support provided for the neck by both sides of the posterior mandibles 17a.

The two support members 121 and 122 are configured as cantilevers which project upwardly and inwardly toward the user's chin 16, and more particularly towards the mandible 17. The ends of the two support members 121 and 122 are configured to have large profiled contact areas to provide rest members 27. The two support members 121 and 122 are positioned to make contact with the user's posterior mandibles 17a when the head 13 is in an upright position or tilted forwarded slightly to an extent deemed acceptable. The two support members 121 and 122 are resiliently flexible. This feature is achieved through the configuration of the support members 121 and 122 and the characteristics of the plastics material from which it is formed.

As the user 11 moves his or her head forwards, the support portion 23 yielding resists the forward tilting of the head. The yielding resistance is achieved by the deforming of the two support members 121 and 122 through resilient flexion under the force exerted upon them by the user's the posterior mandibles 17a. Once the force exerted upon the two support members 121 and 122 ceases, the support members will revert back to their original form and position. The yielding resistance allows the patient to strengthen the muscles supporting the cervical vertebrae with active exercise.

Referring now to FIGS. 22 to 27, there is shown a sixth embodiment of a neck support apparatus 10 according to the invention. The sixth embodiment is similar in some respects to the first embodiment and corresponding reference numerals are used to identify corresponding parts where appropriate.

Figure 22:
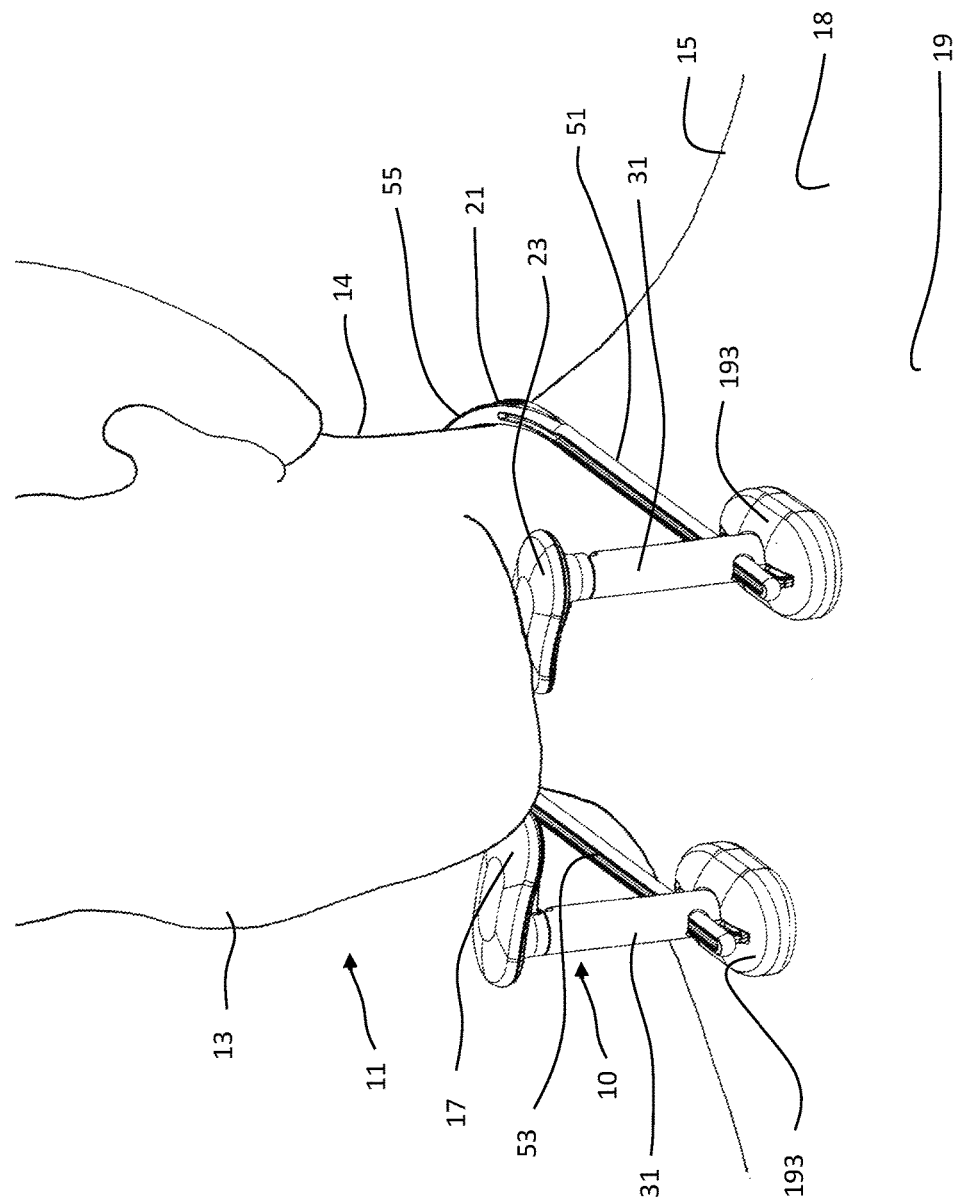
FIG. 22 is a schematic perspective view of a sixth embodiment of a neck support apparatus according to the invention, with the apparatus shown fitted onto a user.

In this sixth embodiment, the neck support apparatus 10 comprises base portion 21 for positioning on a part of the body of the user 11 and support portion 23 extending from the base portion and incorporating rest 25. In the arrangement illustrated, the rest 25 comprises two rest members 27 upon and between which the underside of the posterior mandibles of the user 11 can rest, as illustrated in FIG. 22.

Each rest member 27 comprises a base section 28 and a support section 29 which presents a surface upon which the underside of the posterior mandibles of the user can rest. The support section 29 may be padded or otherwise provide with cushioning to increase comfort at the point of contact with the mandible.

The support portion 23 further comprises two struts 31 which are mounted on the base portion 21 and on which the rest members 27 are mounted. More particularly, each strut 31 has an inner end section 32 adapted for connection to the base portion 21 and an outer end section 33 adapted for connection to the respective rest member 27.

In this embodiment, the base portion 21 comprises a yoke structure 51 having two limb portions 53 and a bridge portion 55 extending between the two limb portions at common ends thereof. In the arrangement illustrated, the yoke structure 51 is configured as an inverted U-shape. The free ends 57 of the two limb portions 53 define an opening 59 through which the neck 14 of the user 11 can be received to allow positioning of the yoke structure 51 on the upper torso 18 of the user 11, with the bridge portion 55 extending behind the neck 14 and the two limb portions 53 resting on, and extending forwardly from, the shoulders 15 in front of the upper torso 18 of the user, as shown in FIG. 22.

The two limb portions 53 and the bridge portion 55 are of unitary construction in this embodiment. Other arrangements are possible; for example, two limb portions 53 and the bridge portion 55 may be formed of sections detachably connected together.

Figure 23:
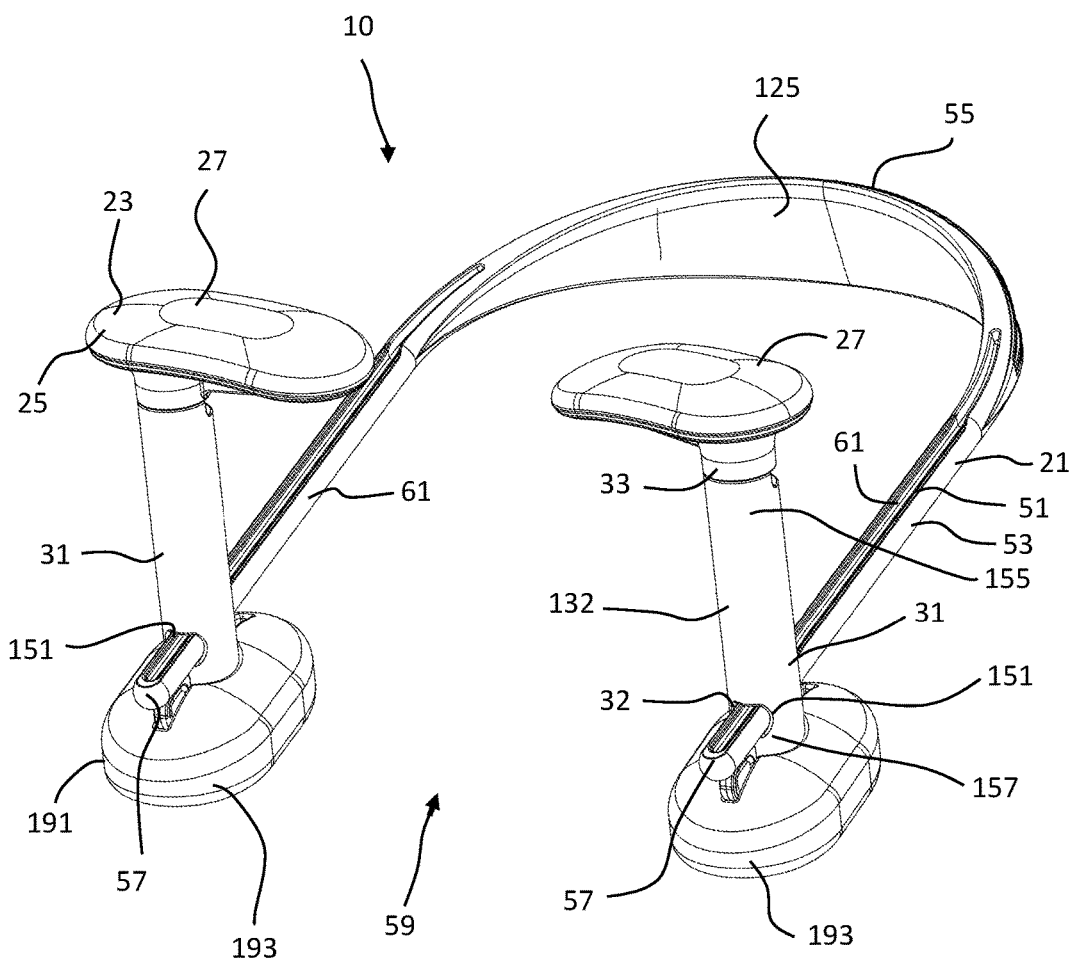
FIG. 23 is a schematic perspective view of the neck support apparatus shown in FIG. 22.

In the arrangement shown, the bridge portion 55 is configured to present a broad contact surface 125 to face the rear of the neck 14 of the user 11. In this regard, the bridge portion 55 is configured to progressively increase in size in the direction away from the two limb portions 53, as best seen in FIG. 23.

The yoke structure 51 may be formed of light-weight material, such as a plastics material; for example, a thermoplastics material such as polycarbonate-ABS. Other materials may also be appropriate, such as, a light-weight metal such as aluminium, or a combination of such materials.

In this embodiment, the yoke structure 51 is constructed to be firm yet resiliently flexible; for example, the yoke structure 51 may comprise an elongate member formed of resiliently deformable material into a U-shape configuration. The aforementioned thermoplastics material such as polycarbonate-ABS may be a suitable material for the elongate element. Specifically, the yoke structure 51 is sufficiently firm so as to ordinarily retain the two limb portions 53 and the bridge portion 55 fixed in position with respect to each other, and also support loadings imposed thereon, while in use supporting the head 13 of the user 11. Further, the yoke structure 51 is sufficiently flexible to facilitate temporary adjustment by deformation, such as bending, to allow the opening 59 between the two limb portions 53 to be selectively expanded to facilitate positioning of the yoke structure around the neck 14 of the user 11.

The struts 31 are mounted on the two limb portions 53 of the yoke structure 51. In particular, each strut 31 is adjustably mounted on a respective one of the two limb portions 53. The adjustable mounting of each strut 31 on the respective limb portion 53 of the yoke structure 51 allows selective displacement of the strut along the limb portion for varying the position at which the strut is attached to the limb portion. With this arrangement, each limb portion 53 provides rail 61 along which the strut is selectively slidable. Each limb portion 53 has an upper longitudinal side which may incorporate a longitudinal channel 127 provided for weight reduction purposes. Each limb portion 53 has a lower longitudinal side which incorporates a longitudinal channel 129, the purpose of which will be explained later. The longitudinal channel 129 presents a curved profile in cross-section.

In this embodiment, the inner end section 32 of each strut 31 is configured to provide mounting portion 63 for engagement with the rail 61 in a manner permitting slidable movement with respect to the rail, and a locking mechanism 65 for locking the mounting portion 63 in a selected position with respect to the rail, as will be described in more detail later.

Figure 24:
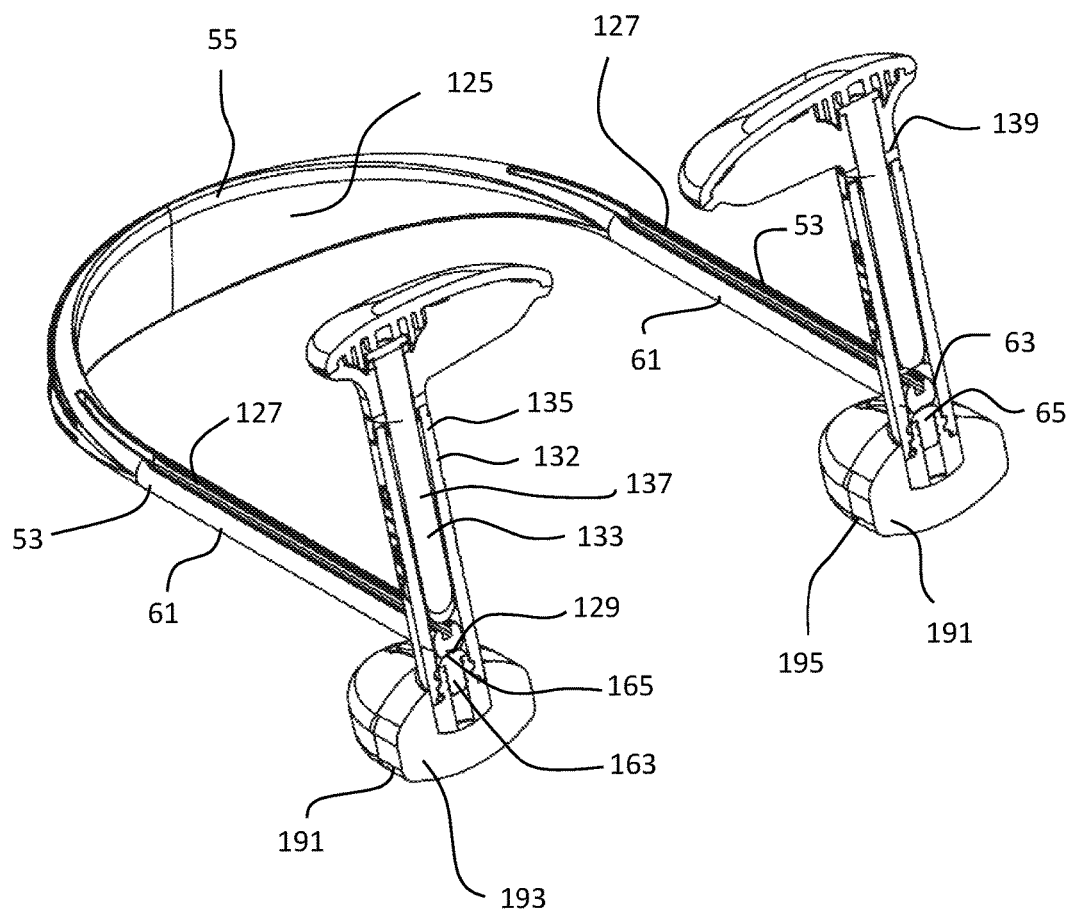
FIG. 24 is a partly-sectioned schematic perspective view of the neck support apparatus shown in FIG. 22.
Figure 26:
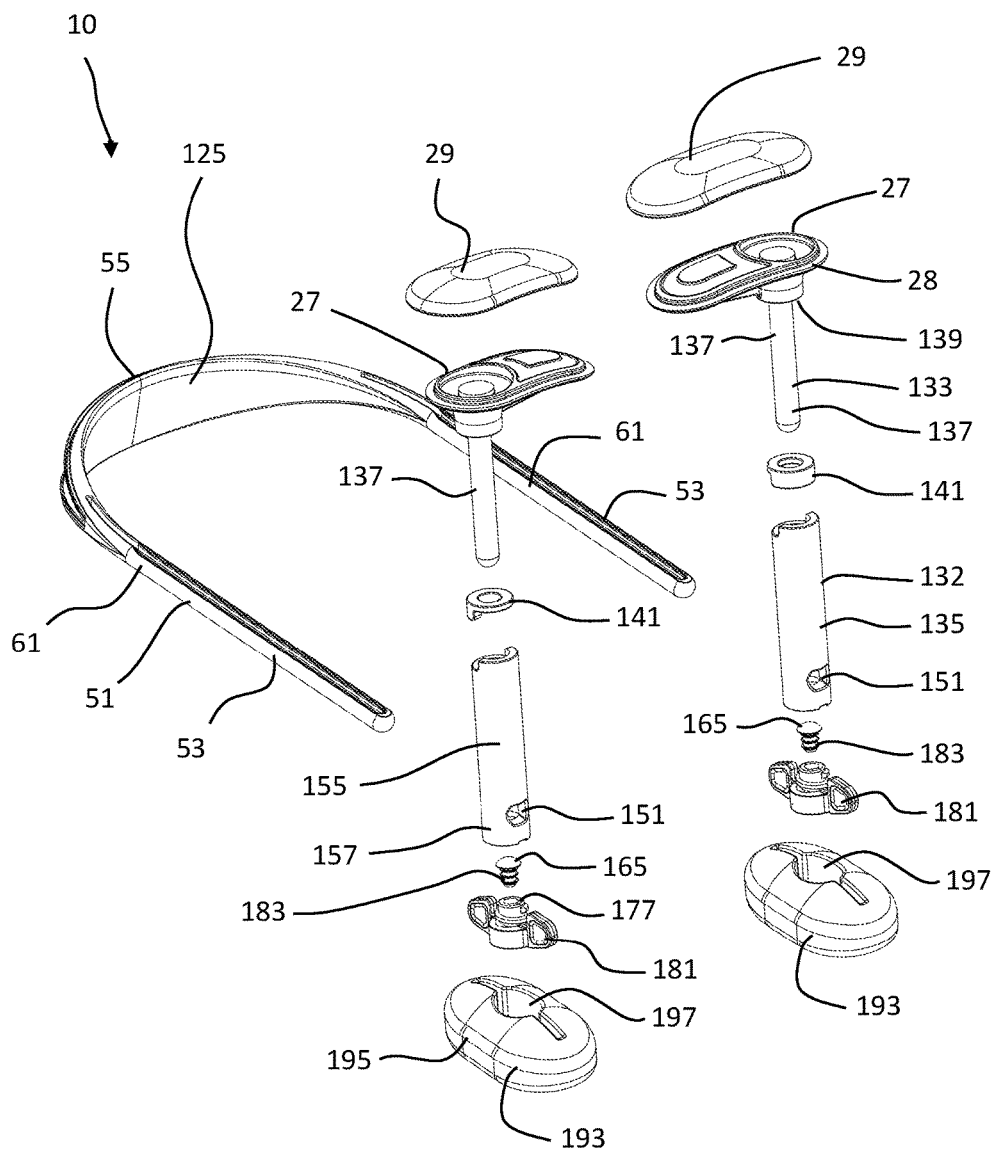
FIG. 26 is a schematic perspective view of the neck support apparatus shown in FIG. 22 depicted in exploded form.

In this embodiment, each strut 31 comprises an outer strut section 132 and an inner strut section 133. The outer strut section 132 is configured as a sleeve 135 and the inner strut section 133 is configured as a post 137 receivable in the sleeve. The two rest members 27 are mounted on the struts, with each rest member being mounted on the upper end of one of the posts 137. In the arrangement shown, each post 137 is integrated at its upper end with the respective rest member 27 so as to depend therefrom, as best seen in FIGS. 24 and 26. Each rest member 27 presents a shoulder 139 extending about the post 137 for location on the upper end of the outer strut section 132 or any intervening spacer. In the arrangement shown, there is an intervening spacer 141 provided between the shoulder 139 of the rest member 27 and the upper end of the outer strut section 132. The spacer 141 is provided for varying the effective length of sleeve 135 defining the outer strut section 132, and thereby the effective length of the strut 31. Typically, the support apparatus 10 would be provided with a variety of spacers 141 as pairs in different sizes to accommodate a range of available lengths for the struts 31, according to the requirements of the user.

There may be provision for locking the rest member 27 against relative rotation with respect to the strut 31 when in position on the strut. In the arrangement shown, such provision is by way of interlocking lugs, one associated with the shoulder 139 of the rest member 27, and the other associated with the upper end of the outer strut section 132 or any intervening spacer 141. With this arrangement, the rest member 27 (together with the post 137 integrated with it) can only be rotated with respect to the outer strut section 132 when the post is received in the sleeve 135 and the respective lugs 143 are out of locking engagement with each other. When the rest member 27 is orientated correctly with respect to the strut 31 so as to be appropriately positioned to afford support for the user (as shown in FIGS. 22 and 23), the lugs are in locking engagement with each out, thereby retaining the rest members in the desired orientation. The lugs can be moved into an out of locking engagement by simply lowering and lifting the rest member 27 when the post 137 is received within the sleeve 1135.

The mounting portion 63 provided at the inner end section 32 of each strut 31 comprises a transverse mounting hole 151 provided in the outer strut section 132 at a location spaced inwardly from the bottom end 153 of the strut. The mounting hole 151 is sized and shaped to snugly receive the respective limb portion 53 of the yoke structure 51 in a manner permitting sliding movement of the outer strut section 132 along the limb portion. This facilitates adjustment in the position of the strut 31 along the rail 61, as will be described in more detail later.

The presence of the transverse mounting hole 151 in the outer strut section 132 divides the sleeve 135 into an upper sleeve section 155 above the mounting hole and a lower sleeve section 157 below the mounting hole. With this arrangement, the post 137 defined by the inner strut section 133 is received within the upper sleeve section 137, as best seen in FIG. 24. The post 137 does not extend down to the mounting hole 151 and consequently does not contact the rail 51.

Figure 25:
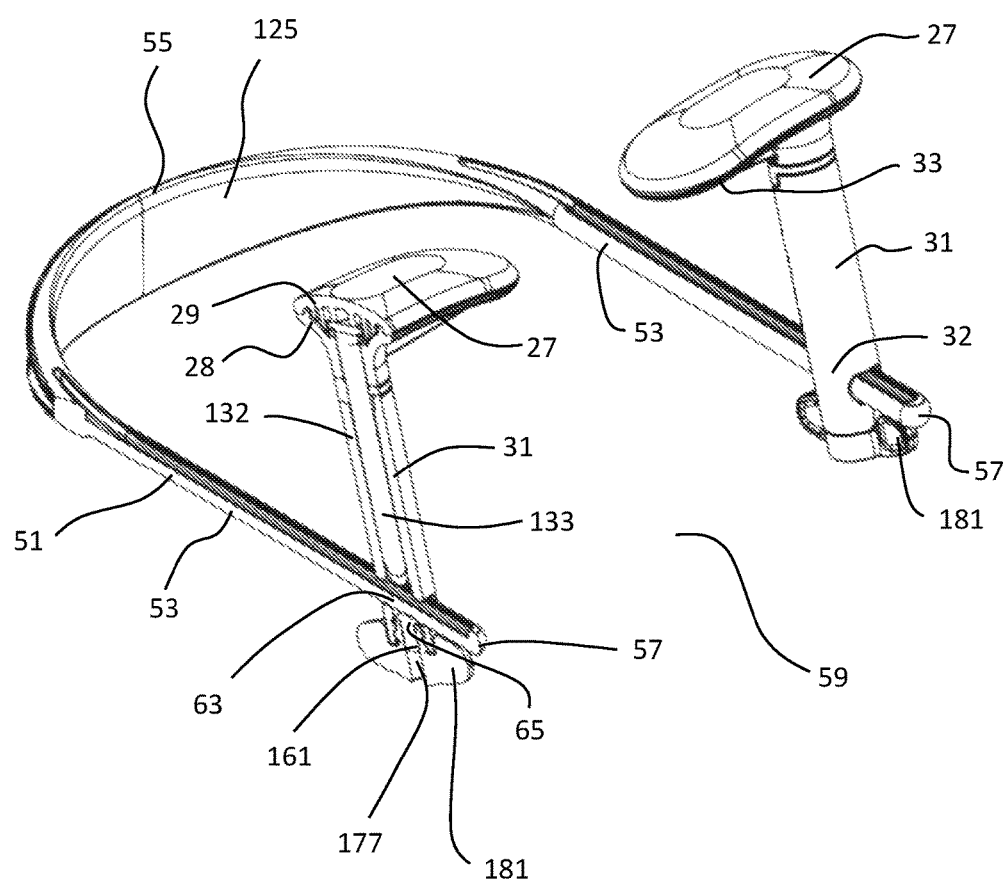
FIG. 25 is a further partly-sectioned schematic perspective view of the neck support apparatus shown in FIG. 22.

The locking mechanism 65 for locking the mounting portion 63 in a selected position with respect to the rail 61 comprises a clamping mechanism 161 associated with the lower sleeve section 157 of the strut 31, as best seen in FIG. 25.

The clamping mechanism 161 comprises a clamping member 163 presenting a bearing surface 165 selectively movable into and out of bearing contact with the lower longitudinal side of that portion of the rail 61 extending through mounting hole 151 in the outer strut section 132. When the bearing surface 165 is in bearing contact with the lower longitudinal side of that portion of the rail 61, it exerts a transverse force on the rail, urging the rail into frictional engagement with the opposed side of the mounting hole 151. In this way, the rail 61 is frictionally clamped between the bearing surface 165 and the opposed side of the mounting hole 151, thereby restraining the strut 31 at the selected position with respect to the rail.

In this embodiment, the clamping member 163 comprises shank 177 in threaded engagement within the lower sleeve section 157 below the mounting hole 151. The shank 177 has an inner end adjacent the mounting hole 151 defining the bearing surface 165 and an outer end configured to receive torque for rotating the shank, whereby the bearing surface 165 can be causes to move towards or away from the mounting hole (and thereby the rail 61 received therein) according to the direction of rotation of the shank. In the arrangement shown, the outer end of the shank 177 extends beyond the sleeve 135 and is configured as a wing nut 181 to facilitate turning of the shank manually, and thereby manual operation of the clamping mechanism 161.

In the arrangement shown, the bearing surface 165 is defined by an insert 183 fitted onto the shank 177 at the inner end thereof.

The bearing surface 165 is configured to mate with longitudinal channel 129 on the lower side of the limb portion 53, as best seen in FIG. 24. In the arrangement shown, the bearing surface is of a dome configuration to conform to the curved cross-sectional profile of the longitudinal channel 129 on the lower side of the limb portion 53.

In this embodiment, the base portion 21 further comprises a contact section 191 associated with each limb portion 53 of the yoke structure 51 for engaging the body of the user. The contact section 191 is associated with the respective strut 31. More particularly, in this embodiment, the contact section 191 is located at the bottom end 153 of the strut. The contact section 191 comprises a contact pad 193. In the arrangement shown, the contact pad 193 is adapted to be located at the bottom end 153 of the strut 31 around the exterior part of the clamping mechanism 161, particularly the wing nut 181. For this purpose, the contact pad 193 comprises a pad body 195 comprising resiliently deformable material and an aperture 197 in the pad body configured to receive removably the exterior part of the clamping mechanism 161. With this arrangement, the contact pad 193 can be selectively removed to provide access as required to the clamping mechanism 161. The contact pads 193 have been removed in the arrangement shown in FIG. 35 so as to reveal the wing nuts 181.

When the neck support apparatus 10 according to this embodiment is in use, some of loading on the rest members 27 can be transmitted through the struts 31 to the contact pads 193 and then onto the torso of the use. The provision of contact pads 193 may also facilitate more stability of the neck support apparatus 10 on the user. Further, the provision of contact pads 193 may also afford more comfort for the user, particularly in the collar bone area where discomfort might otherwise occur through contact with the yoke structure 51.

The neck support apparatus 10 of this embodiment may be of collapsible construction to provide a compact arrangement for transportation and storage, as was the case with the first embodiment. In particular, the struts may be selectively rotatable into a collapsed condition in which they are folded inwardly towards the base portion to rest upon or closely adjacent the base portion. Additionally, various component parts of the apparatus 10 may be disassembled for transportation and storage.

Figure 27:
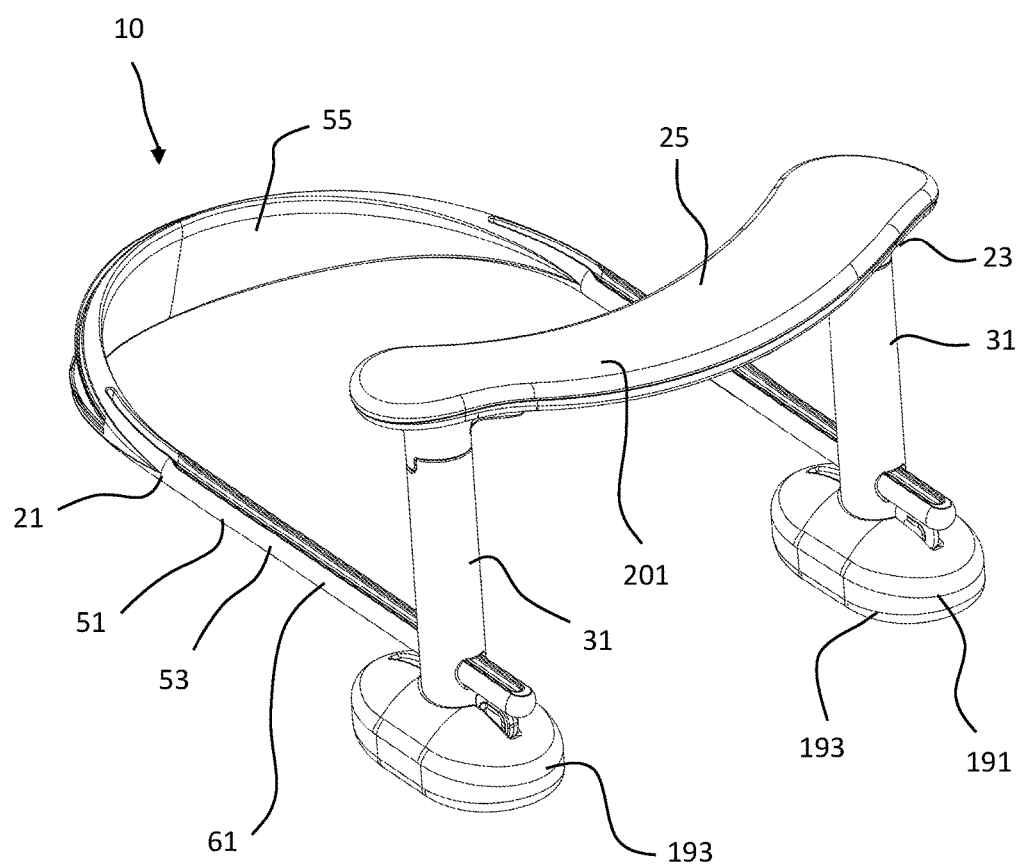
FIG. 27 is a schematic perspective view of a seventh embodiment of a neck support apparatus according to the invention.

Referring now to FIG. 27, there is shown a seventh embodiment of a neck support apparatus 10 according to the invention. The seventh embodiment is similar in some respects to the sixth embodiment and corresponding reference numerals are used to identify corresponding parts where appropriate.

In this seventh embodiment, the rest 25 comprises a single rest member 201 supported by, and extending between, the two struts 31, rather than two separate rest members 27. The use of the single rest member 201 may provide advantages in certain circumstances as is offers a rigid connection between the two struts 31, thereby providing a neck support apparatus which is likely to be more rigid when in use. In particular, the rigid connection between the two struts 31 may assist in preventing unintended deformation of the yoke structure 51, and specifically the limb portions 53, when under load in use.

The neck support apparatus of this seventh embodiment may require more manipulation to fit onto, and remove from, a user than the neck support apparatus of the sixth embodiment owing to the unitary construction of the single rest member 201.

It is a feature of the sixth and seventh embodiments that the two rest portions 27 and the single rest member 201 can be used interchangeably between the two embodiments.

Referring now to FIGS. 28 to 33, there is shown an eighth embodiment of a neck support apparatus 10 according to the invention. The eighth embodiment is similar in some respects to the sixth embodiment and corresponding reference numerals are used to identify corresponding parts where appropriate.

In this eighth embodiment, the rest 25 comprises two rest portions 211, 212 adapted to be releasably connected together provide an integrated rest structure 213 supported by, and extending between, the two struts 31. Each rest portion 211, 212 is associated with a respective one of the two posts 137, as was the case with the two rest members 27 in the sixth embodiment. However, unlike the two rest members 27 in the sixth embodiment, the two rest portions 211, 212 are adapted to be releasably connected together provide the integrated rest structure 213.

Figure 28:
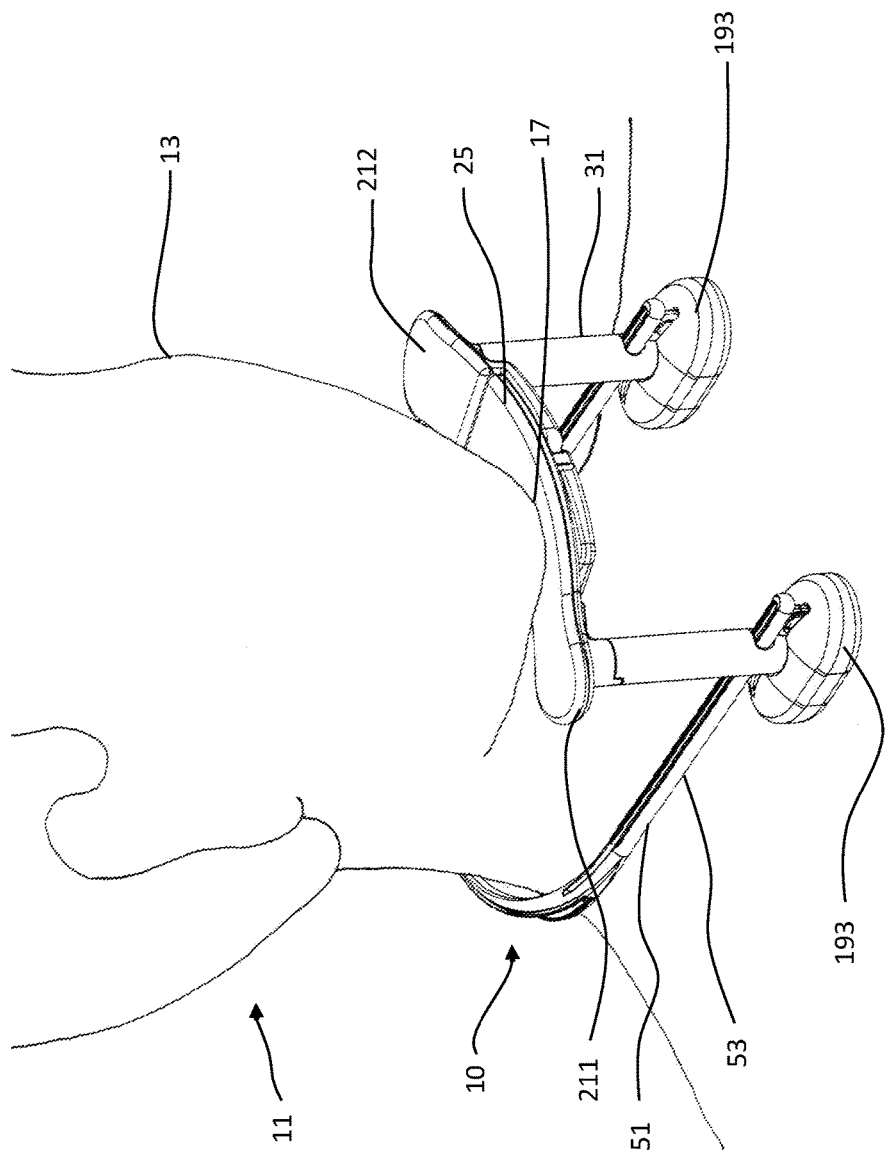
FIG. 28 is a schematic perspective view of eight embodiment of a neck support apparatus according to the invention, with the apparatus shown in a first condition fitted onto a user.

With this arrangement, the two rest portions 211, 212 are selectively movable between first and second conditions. In the first condition, the two rest portions 211, 212 cooperate to provide the integrated rest structure 213 to receive and support the mandible of the user, as shown in FIG. 28. In the second condition, the two rest portions 211, 212 are in spaced apart relation to facilitate placement of the support portion 23 on the user. In other words, in the second condition, the two rest portions 211, 212 are sufficiently clear of the open front 59 of the yoke structure 51 so as not to impede placement of the yoke structure onto, and removal of the yoke structure from, a user. The two rest portions 211, 212 are shown in the second condition in FIG. 32.

The two rest portions may be adapted to be releasable connected together in the first condition to provide the integrated rest structure 213 to receive and support the mandible of the user, the integrated rest structure being supported by and extending between the two struts 31.

In this embodiment, the two rest portions 211, 212 are adapted to swing between the first and second conditions. The construction of the struts 31, featuring the posts 137 being received on the sleeves 135 in a manner permitting relative rotation, facilitates the swinging action.

Figure 30:
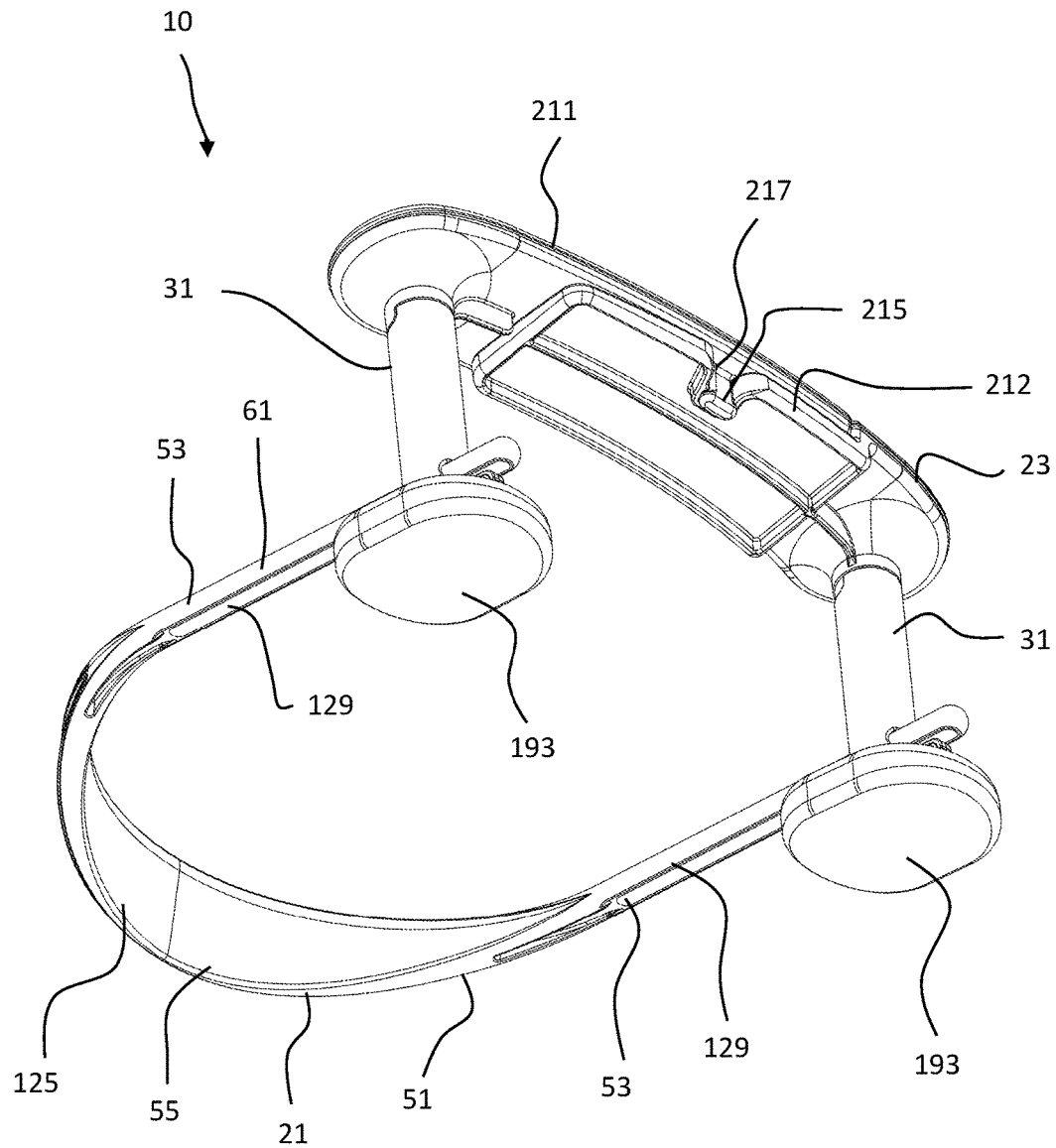
FIG. 30 is a view similar to FIG. 29 but from the underside.
Figure 31:
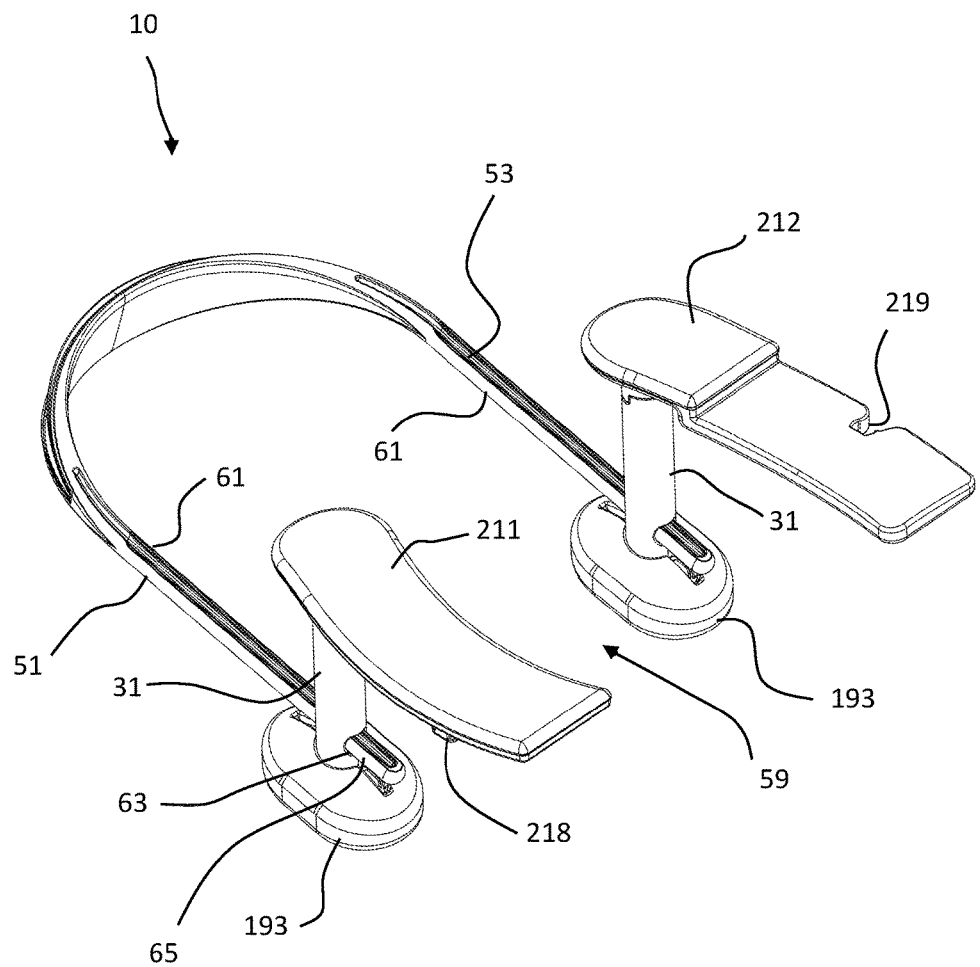
FIG. 31 is a schematic perspective view of the neck support apparatus shown in FIG. 28 depicted in a second condition.
Figure 32:
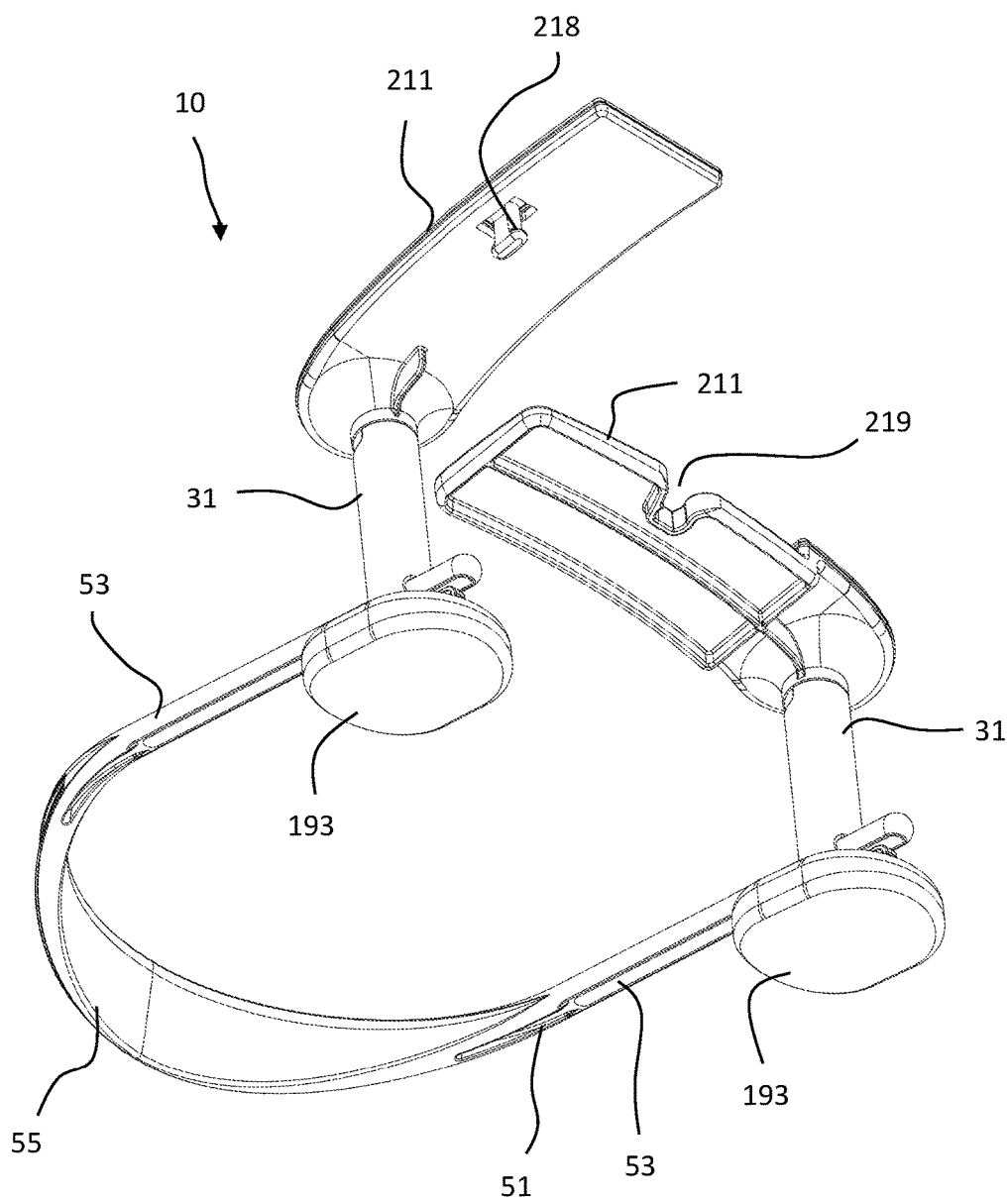
FIG. 32 is a schematic perspective view of the neck support apparatus shown in FIG. 28 depicted with one rest portion in position corresponding to the first condition and the other rest portion in position corresponding to the second condition.
Figure 33:
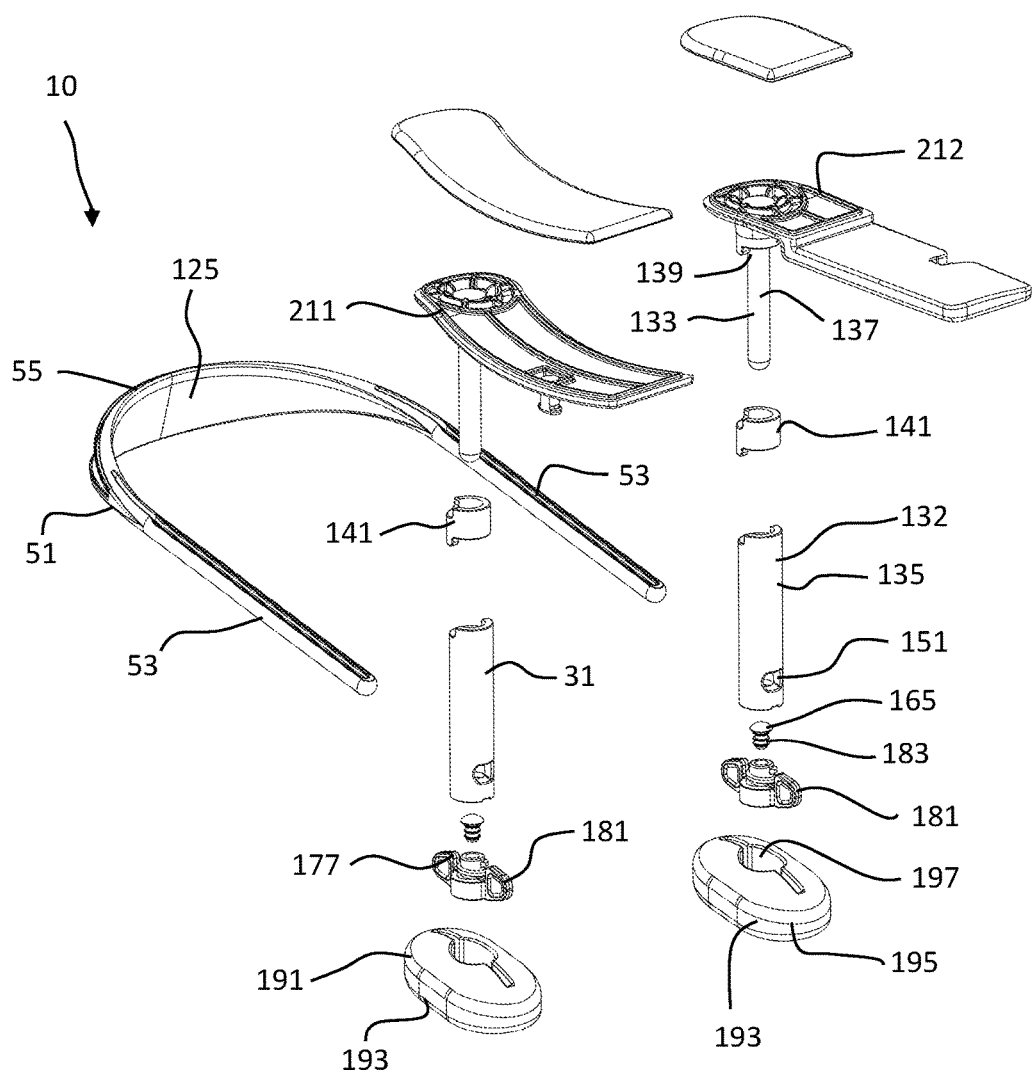
FIG. 33 is a schematic perspective view of the neck support apparatus shown in FIG. 28 depicted in exploded form.

The two rest portions 211, 212 can be releasably connected together in any appropriate way to provide the integrated rest structure 213. In the arrangement shown, the two rest portions 211, 212 are configured to come together in partly overlapping relation and to be releasably interconnected by a lock 215. The lock 215 may comprise a snap lock mechanism 217 comprising a male lock portion 218 on one rest portion 211 and a mating female lock portion 219 on the other rest portion 212, with the two portions being adapted to interlock when the two rest portions 211, 212 are moved onto the first condition, as best seen in FIG. 30. Typically, rest portion 212 having the female lock portion 219 would initially be swung into a position corresponding to the first condition, as shown in FIG. 32, and thereafter rest portion 211 having the male lock portion 218 then swung into a position corresponding to the first condition. The two rest portions 211, 212 can then be releasably connected together using the snap lock mechanism 217.

Figure 29:
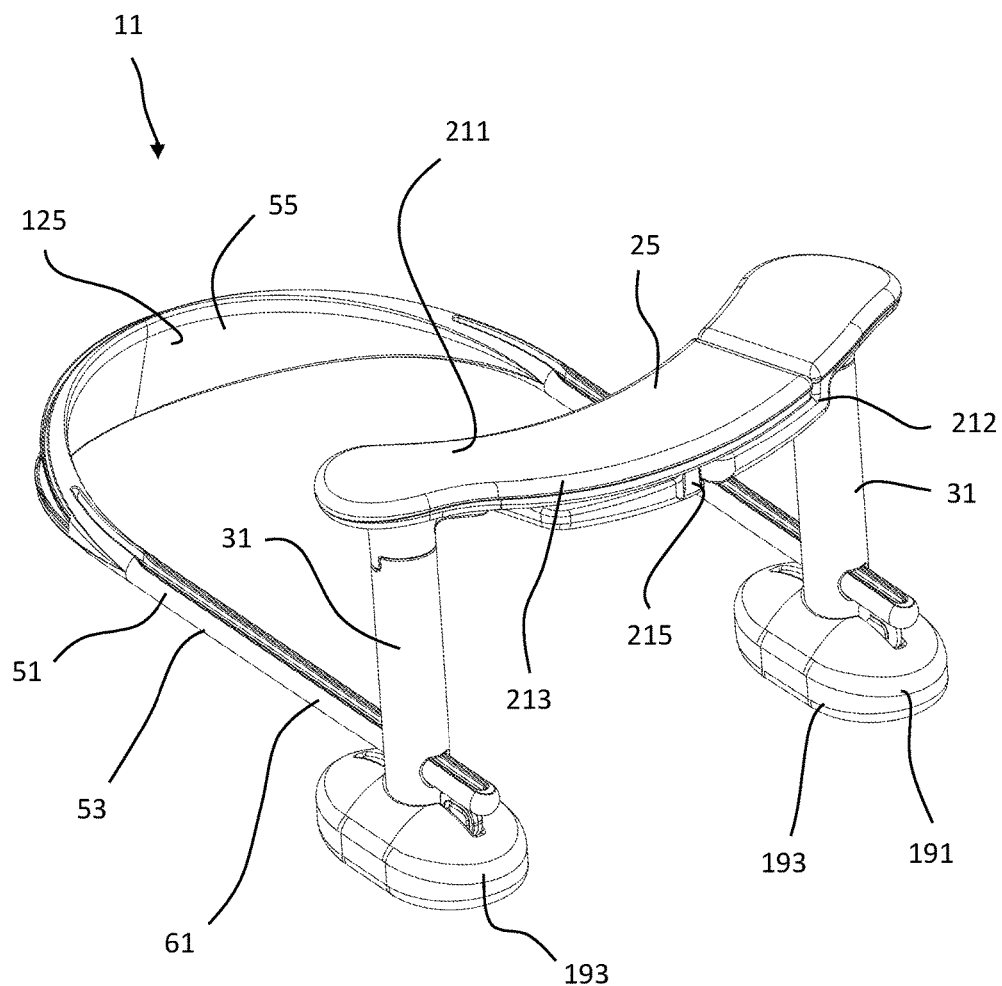
FIG. 29 is a schematic perspective view of the neck support apparatus shown in FIG. 28.

The feature whereby the two rest portions 211, 212 are configured to come together in partly overlapping relation, as best seen in FIGS. 29 and 30, is advantageous as it promotes stability of the integrated rest structure 213.

It is a feature of this eight embodiment that the two rest portions 211, 212 can be used interchangeably with the two rest portions 27 and the single rest member 201 of the two previous two embodiments.

From the foregoing it is evident that the present invention provides a relatively simple yet highly effective neck support apparatus. The neck support apparatus according to the invention is advantageous as it does not adversely obstruct the field of vision of a user. In particular, the arrangement facilitates support for, and positioning of, the rest in a manner which is less intrusive and more aesthetically pleasing than current neck supporting devices. Further, it is believed that the arrangement is not too bulky or cumbersome aesthetically to deter use of the support apparatus. Still further, it is believed that the arrangement is likely to be less invasive and more comfortable to wear that the prior art neck braces and collars referred to above. Accordingly it is believe that users are more likely wear the neck support apparatus according to the invention as prescribed.

While the present invention has been described in terms of a preferred embodiments in order to facilitate better understanding of the invention, it should be appreciated that various modifications can be made without departing from the principles of the invention. Therefore, the invention should be understood to include all such modifications within its scope.

Furthermore, it should be understood that any feature described in relation to one embodiment may, as and when appropriate, be incorporated in any other embodiment even though the feature may not have necessarily been described and illustrated in relation to that other embodiment.

Reference to positional descriptions, such as "upper", "lower", "top", "bottom", "front", "back" "forward" and "rearward", are to be taken in context of the embodiments depicted in the drawings, and are not to be taken as limiting the invention to the literal interpretation of the term but rather as would be understood by the skilled addressee.

Further, reference to anatomical descriptions, such as "mandible" and "posterior mandibles", are to be taken in context of the embodiments depicted in the drawings, and are not to be taken as limiting the invention to the literal interpretation of the term but rather as would be understood by the skilled addressee.

Additionally, where the terms "system", "device", and "apparatus" are used in the context of the invention, they are to be understood as including reference to any group of functionally related or interacting, interrelated, interdependent or associated components or elements that may be located in proximity to, separate from, integrated with, or discrete from, each other.

Throughout this specification, unless the context requires otherwise, the word "comprise" or variations such as "comprises" or "comprising", will be understood to imply the inclusion of a stated integer or group of integers but not the exclusion of any other integer or group of integers.

The invention claimed is:

1. A support apparatus comprising a base portion for positioning on a part of the body of a user, and a support portion extending from the base portion and adapted to support the user's mandible, wherein the support portion comprises two rest portions, each rest portion mounted on a strut extending from the base portion, wherein the two rest portions are selectively movable relative to one another between first closed and second open conditions, wherein in the first closed condition the two rest portions are releasably and directly connected together to receive and support the mandible of the user, wherein in the second open condition the two rest portions are in spaced apart relation to facilitate placement of the support portion on the user, and wherein the two rest portions are adapted to be releasably and directly connected together in the first closed condition to provide an integrated rest structure to receive and support the user's mandible.

2. The support apparatus according to claim 1 wherein each strut is selectively variable in length.

3. The support apparatus according to claim 1 wherein the struts are adjustable in position with respect to the base portion.

4. The support apparatus according to claim 1 wherein the base portion is adapted to be positioned on the upper torso of the user over the shoulders of the user.

5. The apparatus according to claim 1 wherein the base portion is configured as a yoke structure having two limb portions and a bridge portion extending between the two limb portions at common ends thereof.

6. The apparatus according to claim 5 wherein the free ends of the two limb portions define an opening through which the neck of the user can be received to allow positioning of the yoke structure on the upper torso of the user, with the bridge portion extending behind the neck of the user and the two limb portions extending forwardly thereof over the shoulders of the user.

7. The apparatus according to claim 6 wherein the struts are mounted on the two limb portions of the yoke structure.

8. The apparatus according to claim 7 wherein each limb portion provides a rail along which the respective strut is selectively movable.

9. The apparatus according to claim 8 wherein each strut comprises a mounting portion configured for engagement with the rail in a manner permitting selective movement of the strut with respect to the rail, and wherein each strut further comprises a locking mechanism for releasably locking the mounting portion in a selected position with respect to the rail.

10. The apparatus according to claim 9 wherein the mounting portion is integrated with the respective strut.

11. The apparatus according to claim 9 wherein the locking mechanism is integrated with the respective strut.

12. The apparatus according to claim 9 wherein the mounting portion comprises a transverse mounting hole provided in the strut to receive the rail in a manner permitting sliding movement of the strut along the rail, and wherein the locking mechanism comprises a clamping member selectively movable into and out of bearing contact with that portion of the rail extending through the mounting hole to urge the rail into frictional engagement with an opposed side of the mounting hole and frictionally clamp the strut with respect to the rail.

13. The apparatus according to claim 5 wherein the base portion further comprises a contact section associated with each limb of the yoke for engaging the body of a user.

14. The apparatus according to claim 13 wherein the contact section is associated with the respective strut.

15. The apparatus according to claim 14 wherein the contact section comprises a contact pad disposed on the underside of the respective strut.

16. The apparatus according to claim 1 wherein the struts are selectively movable into a collapsed condition in which they are folded inwardly towards the base portion to rest upon or closely adjacent the base portion.

17. The apparatus according to claim 1 wherein the support portion includes a resiliently deformable section adapted to yieldingly resist forward tilting of the head of the user.

18. The apparatus according to claim 17 further comprising provision for counting or otherwise identifying the number of occurrences in which the support portion yieldingly resists forward tilting of the head.

19. The apparatus according to claim 1 wherein various component parts of the apparatus are adapted to be collapsed for transportation and storage of the apparatus.

* * * * *